United States Patent
Federico et al.

(10) Patent No.: US 6,429,009 B1
(45) Date of Patent: Aug. 6, 2002

(54) COMPOSITION AND METHOD OF IMPARTING RESISTIVITY TO HIV SUPERINFECTION TO CELLS

(75) Inventors: Maurizio Federico; Paola Verani, both of Rome; Fulvio Mavilio; Giuliana Ferrari, both of Milan, all of (IT)

(73) Assignees: Istituto Superiore Disanita', Rome; Fondaxione Centro San Raffaele; del Monte Tabor GenEra S.p.A., both of Milan, all of (IT)

(*) Notice: Subject to any disclaimer, the term of this patent is extended or adjusted under 35 U.S.C. 154(b) by 0 days.

(21) Appl. No.: 09/051,231

(22) PCT Filed: Oct. 8, 1996

(86) PCT No.: PCT/IT96/00185
§ 371 (c)(1),
(2), (4) Date: Apr. 8, 1998

(87) PCT Pub. No.: WO97/13861
PCT Pub. Date: Apr. 17, 1997

(30) Foreign Application Priority Data

Oct. 9, 1995 (IT) .................................... RM95A0667

(51) Int. Cl.[7] .............................................. C12N 15/00

(52) U.S. Cl. ............................. 435/320.1; 424/188.1; 424/208.1

(58) Field of Search ................. 435/5; 424/188.1, 424/208.1; 536/23.72, 24.1

(56) References Cited

PUBLICATIONS

Feinberg, M.B. and D. Trono, 1992, "Intracellular immunization: trans–dominant mutants of HIV gene products as tools for the study and interruption of viral replication", AIDS Res. Human Retro. 8(6):1013–1022.*

Keller, G., et al., 1985, "Expression of a foreign gene in myeloid and lymphoid cells derived from multipotent haematopoietic precursors", Nature 318:149–154.*

*Journal of General Virology*, vol. 72, No. 5, May, 1998, pp. 4308–4319, Federico et al.: "gag, vif, and nef, Genes Contribute by a Nonproducer Human Immunodeficiency Virus Type 1 (HIV–1) Variant: Indentification of Novel HIV–1–Inhibiting Viral Protein Mutants."

(List continued on next page.)

*Primary Examiner*—Laurie Scheiner
*Assistant Examiner*—Jeffrey S. Parkin
(74) *Attorney, Agent, or Firm*—Smith, Gambrell & Russell, LLP

(57) ABSTRACT

The invention describes the expression of a human immunodeficiency virus (HIV) type 1 provirus (F12-HIV) cloned from a nonproducer, chronically-infected CD4 down-regulated Hut-78 cell clone (F12) which does not lead to the formation of viral particles and, upon transfection in HeLa CD4+ cells, confers resistance to HIV superinfection without affecting CD4 receptor exposure. A Moloney murine leukemia virus-based retroviral vector containing an F12-HIV genome lacking the 3' long terminal repeat (LTR) and part of the nef gene, expressed under the control of its 5' LTR, was constructed to facilitate the transfer of the anti-HIV properties of F12-HIV into human cells. The F12-HIV genome was inserted in an orientation opposite to that of the murine leukemia virus transcriptional unit and was designated the N2/F12-HIV nef⁻ antisense vector. Lymphoblastoid CEMss cells, as well as human peripheral blood lymphocytes, were successfully transduced by the recombinant retrovirus. CEMss clones expressing the F12-HIV nef⁻ antisense vector were resistant to HIV superinfection even at the highest multiplicity of infection tested ($10^5$ 50% tissue culture infective doses per $10^6$ cells). Nonproducer, interfering HIV proviruses transduced into retroviral vectors may provide an alternative strategy for the protection of CD4+ human primary cells from HIV infection.

4 Claims, 15 Drawing Sheets

OTHER PUBLICATIONS

Figure 1:
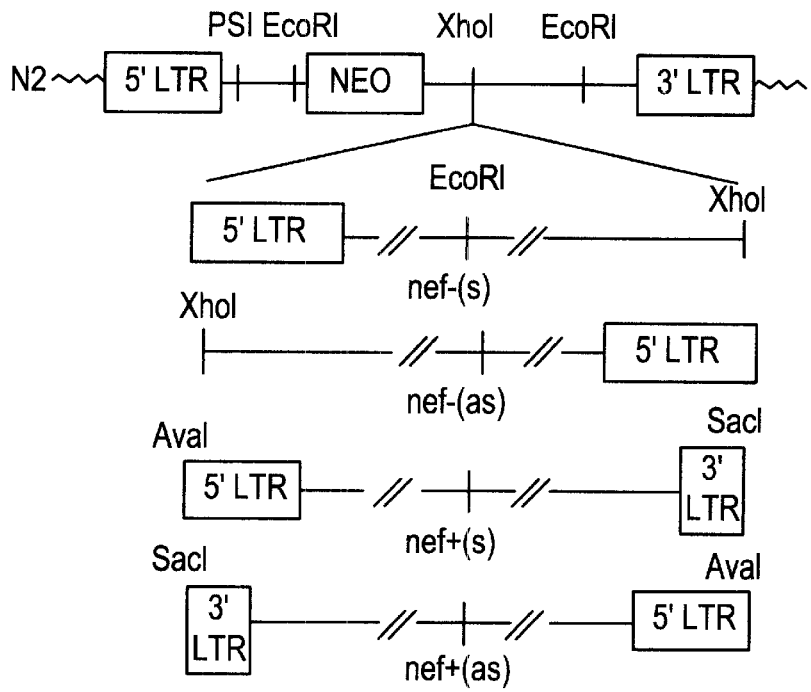

*Journal of General Virology*, vol. 74, 1993, pp. 2099–2110, XP002024028, Federico, et al.: "A Recombinant Retrovirus Carrying a Non–Producer Human Immunodeficiency Virus (HIV) Type 1 Variant Induces Resistance to Superinfecting HIV."

*Journal of General Virology*, vol. 206, 10 1/95, pp. 76–84, XP002024029 Federico, et al.: "Full Expresion of Transfected Nonproducer Interfering HIV–1 Proviral DNA Abrogates Susceptibility of Human He–La CD4+ Cells to HIV."

*Journal of Virology*, vol. 69, No. 11, 11/95, pp. 6618–6626, XP002024030 Federico, et al.: "A Nonproducer, Interfering Human Ummunodeficiency Virus (HIV) Type 1 Provirus Can Be Transduced Through A Murine Leukemia Virus –Based Retroviral Vector: Recovery of an Anti–HIV Mouse/Human Pseudotype Retrovirus."

*Journal of General Virology*, vol. 77, 9/96, pp. 2009–2013, XP002024031, Carlini, et al.: "The Non–Producer Phenotype of the Human Immunodefiency Virus Type 1 Provirus F12/HIV–1 is the Result of Mutiple Genetic Variations."

F. Carlini, et al., "Sequence Analysis of an HIV–1 Proviral DNA from a non Producer Chronically Infected HUT–78 Cellular Clone," J. of Vir. Dis., vol. 1, No. 1, 1995, pp. 40–55.

* cited by examiner

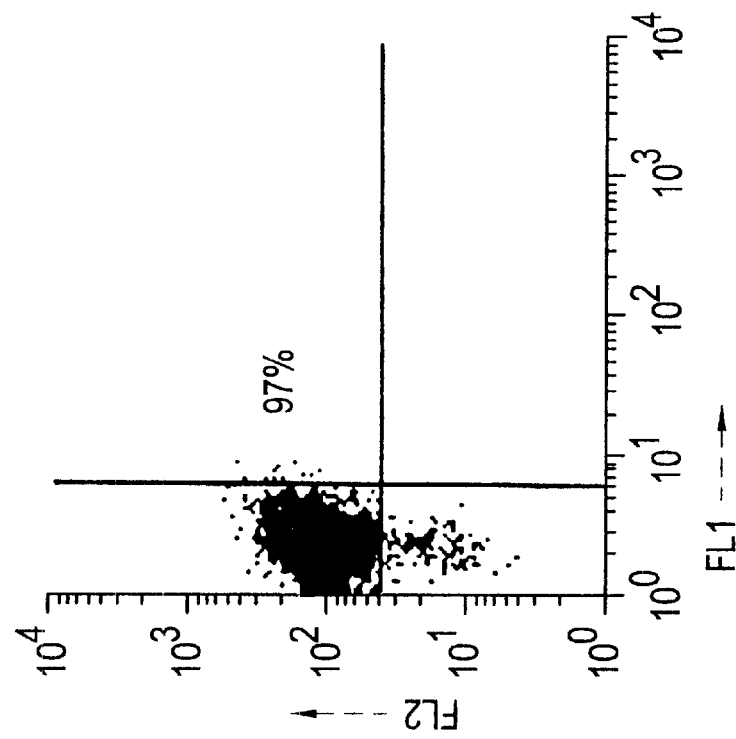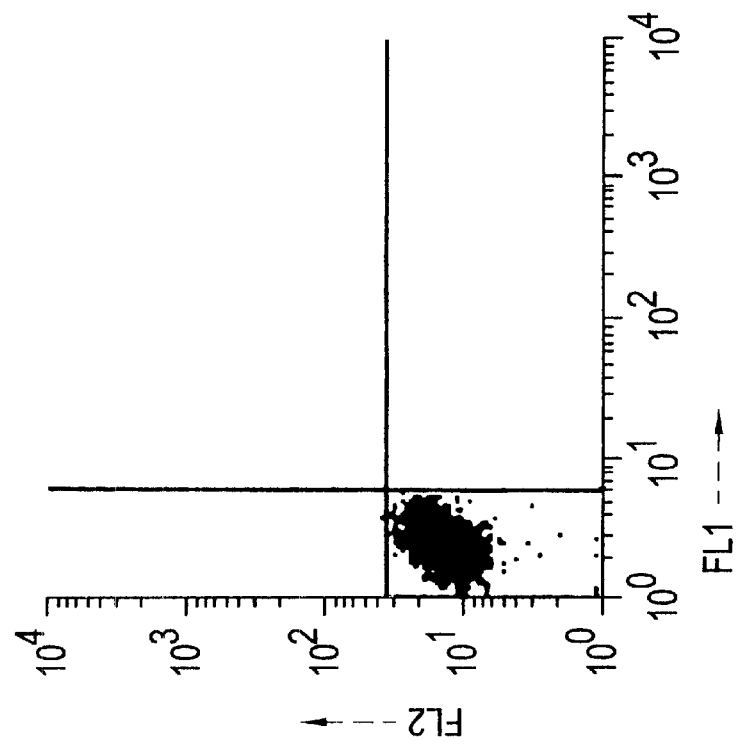

Full length F12/HIV

F12/HIV $U_3$ LTR

F12/HIV nef

F12/HIV env

NEO

U3-MLV

R/U5-MLV psi-MLV

COMPOSITION AND METHOD OF IMPARTING RESISTIVITY TO HIV SUPERINFECTION TO CELLS

The present invention relates to a composition and to a method of imparting resistivity to superinfection with HIV.

More in particular the invention concerns a composition and a method to confer resistance to human cells, in particular T-cells, to the superinfection with a retrovirus, specifically the human immunodeficiency virus (HIV).

Several experimental strategies aimed at blocking HIV replication in vivo have been proposed. So far, most have been based on immunotherapeutic or chemotherapeutic approaches, in which the anti-HIV mechanism of action is well known. However, none of the immunotherapeutic and chemotherapeutic approaches proposed thus far has been demonstrated to effect a resolutive anti-HIV therapy.

The goal of a more recently developed alternative anti-HIV experimental design was to render the target cell resistant to HIV replication through the induction of intracellular immunization (Baltimore, Nature 335: 395–396 (1988)). Inhibition of the superinfecting HIV was, in fact, demonstrated in cells expressing HIV-trans-dominant proteins (Malim et al., J. Exp. Med. 176: 1197–1201 (1992); Green et al., Cell 58:215–223 (1989); Modesti et al., New Biol. 3:759–768 (1991); Trono et al., Cell 59:113–120 (1989), Lisziewicz et al., Annual Meeting, Laboratory of Tumor Cell Biology, Gene Therapy (1993); Buchschacher et al., Hum. Gene Ther. 3:391–397 (1992); Stevenson et al., Cell 83:483–486 (1989); and Liu et al., Gene Therapy 1:32–37 (1994)), HIV genome-directed ribozymes (Yu et al., Gene Therapy 1:13–26 (1994); Lorentzen et al., Virus Genes 5:17–23 (1991); Sioud et al., PNAS USA 88:7303–7307 (1991); Weerasinghe et al., J. Virol. 65:5531–5534 (1991); and Yamada et al., Gene Therapy 1:38–45 (1994)), tat/rev decoys (Sullenger et al., Cell 63:601608 (1990); Sullenger et al., J. Virol. 65:6811–6816 (1991); and Smith et al., UCLA/UCI AIDS Symposium: Gene Therapy Approaches to Treatment of HIV Infection (1993)), or antisense RNA (Rhodes et al., J. Gen. Virol. 71:1965–1974 (1990); Rhodes et al., AIDS 5: 145–151 (1991), Sczakiel et al., J. Virol. 65:468–472 (1991); Joshi et al., J Virol. 65:5524–5530 (1991), and Chatterjee et al., Science 258:1485–1488 (1992)). Moreover, an effective anti-HIV intracellular immunization was achieved by transfecting HIV-susceptible cells with DNA coding for either an anti-gpl60 single chain antibody (Marasco et al., PNAS USA 90:7889–7893 (1993)) or a monoclonal anti-rev single chain variable region (Duan et al., Abstract from the 1994 Annual Meeting, Laboratory of Tumor Cell Biology, Sep. 25–Oct. 1, 1994, MD USA).

The prior art methods, however, suffer from the following disadvantages. Many of the above mentioned methods do not work properly in practice because of the fact that anti-HIV compounds able to target a single step of the HIV replication could easily induce the emergence of HIV resistant mutants. This is a very common biological event, considering the extraordinary ability of HIV to mutate as demonstrated, for example, by the HIV strains resistant to antiretroviral chemical compounds (i.e., AZT, ddI) isolated from AIDS patients treated with such drugs. Consequently, many investigators are attempting to synthesize anti-HIV reagents able to target different steps of the HIV life cycle. In addition, some of the described methods have been demonstrated to be either deleterious for the host cells, or difficult to be effectively applicable in clinical protocols.

The present invention seeks to overcome the disadvantages of the above-described methods. The authors of the invention have set up a method to confer resistivity to human cells, in particular to T-cells, to HIV superinfection, following to a stable integration of an HIV non-infective non-producer genomic variant into at least some of cell nuclear genomes. In order to confer resistivity to human cells to HIV superinfection, the instant invention provides a composition to be used for HIV intracellular immunization, during the AIDS therapy. the invention has several advantages, including an easy way of administration, the lacking of HIV spontaneous reversion of non defective variants from a non producer to a producer phenotype, and the ability to confer a good resistance to superinfection.

Evidence obtained by in vitro experiments indicates that F12-HIV non defective non producer variant expression could inhibit different steps of the wild type HIV superinfecting life cycle. In fact, the authors of the invention have shown a block of the wild-type HIV replication, eithr before or after its own tetrotrascrption, depending on the F12-HIV expressing cells tested. Moreover, no modifications or impairments of the physiologic cell functions were demonstrated in any cells harbouring the F12-HIV genome.

"HIV" is used herein to encompass all designations past and present assigned to those viruses implicated as causative agents of acquired immunodeficiency syndrome (AIDS) and AIDS-related complex (ARC), such as HIV, e.g., HIV-1 and HIV-2, and HTLV, e.g., HTLV-III. By "superinfection" is meant that which is known to and understood by those of ordinary skill in the art, i.e., the ability of a given virus to infect a cell already infected by a virus. By "resistivity" is meant the capacity to resist superinfection by a virus, in particular a retrovirus, specifically HIV. By "nondefective" is meant that the genome is complete, whereas by "nonproducer" is meant that viral particles are not produced.

The instant invention providees a composition comprising a retroviral vector comprising a non-defective, non-producer, HIV variant genome, in a sufficient amount to get a stable integration of said non-defective, non-producer, HIV variant genome, in at least some of nuclear genomes of target cells, and the expression of said non-defective, non-producer, HIV variant genome in said target cells, in order to confer resistivity to HIV superinfection to cells, in particular to T cells.

Preferably, the non-defective, non-producer, HIV variant genome integrates in at least the 1% of cell nuclear genomes. More preferably the non-defective, non-producer, HIV variant genome integrates in from about 1% to about 10% of cell nuclear genomes. Preferably the non-defective, non-producer, HIV variant genome is the HIV F12 genome. It is further preferred that the 3' LTR of the F12-HIV genome be deleted prior to insertion into the retroviral vector and that the genome be inserted into the retroviral vector in antisense orientation. A retroviral vector derived from Moloney murine leukemia virus is preferred for the composition of the invention.

A further aspect of the invention provides the use of a retroviral vector comprising a non-defective, non-producer, HIV variant genome in sufficient amount to get a stable integration of the non-defective, non-producer, HIV variant genome into at least some of the nuclear genomes of the cells get in contact with said vector and the expression into said cells of said nondefective, nonproducer HIV variant genome.

Preferably, the non-defective, non-producer, HIV variant genome integrates in at least the 1% of cell nuclear genomes. More preferably the non-defective, non-producer, HIV variant genome integrates in from about 1% to about 10% of cell nuclear genomes. Preferably the non-defective, nonproducer, HIV variant genome is the HIV F12 genome. It is preferred that the 3' LTR of the F12-HIV genome be deleted prior to insertion into the retroviral vector and that the genome be inserted into the retroviral vector in antisense orientation. A retroviral vector derived from Moloney murine leukemia virus is preferred for the composition of the invention.

Alternatively the instant invention provides the use of a composition comprising a retroviral vector a non-defective, non-producer, HIV variant genome to be utilised for the production of a AIDS therapy medicament.

An applicative method of the invention is of imparting resistivity to HIV superinfection to human cells, by means of removing cells from an human, contacting the removed-cells with the composition of the invention in sufficient amount to get a stable integration and the expression of the nondefective, nonproducer HIV variant into at least some of the nuclear genomes of the cells, and reintroducing the so-treated cells to the human-from which the cells had been removed. Such ex vivo methods are described in Ferrari G., Rossini S., Giavazzi R., Maggioni D., Nobili N., Soldati M., Ungers G., Mavilio F., Gilboa E., Bordignon C. "An in vivo model of somatic cell gene therapy for human severe combined immunodeficiency." Science 251: 1363, 1991.

Although, theoretically, any genome from a nondefective, nonproducer HIV variant could be useful or rendered useful in the present inventive method, the genome from the F12-HIV (Dr. M. Federico, Laboratory of Virology, Istituto Superiore di Sanita, Rome).

The F12-HIV variant genome, whose sequence and charcterization is described in Carlini et al. J. Viral Disease 1:40–55 (1992) here wholly incorporated, is characterized by more than 50 mutations, most of which are in the gag, pol , and vif genes and which do not appear to be present in other HIV-1 strains. The mechanism of resistance to superinfection is unknown, and it is conceivable that the resistance is caused either by the expression of a single negative trans-dominant gene product or, more likely, by the concomitant expression of more than one such a product. The exchange of homologous fragments between the F12-HIV variant genome and a wild-type, infectious HIV-1 molecular clone, named pNL4-3 (Dr. M. Martin, AIDS Research and Reference Program, AIDS Program, NIAID, NIH), followed by transfection into HIV-sensitive human cells, indicates that it is necessary to replace at least 6 kb of the genome, between the Bcl I and Xho I restriction sites and encompassing the pol, vif, vpr, vpu, tat, rev, and env genes in order to revert the F12 phenotype from nonproducer to producer. Accordingly, the risk of spontaneous reversion of the nondefective F12-HIV variant from replication-deficient to replication-competent is appreciably low. This risk is further reduced by the absence of the entire 3' LTR and most of the nef gene, both of which are necessary for replication, in the preferred F12-HIV variant constructs. A cell population homogeneously expressing the F12 HIV genome would block any contaminant replication-competent HIV, by the interfering action of the same F12-HIV; this is consistent with evidence that, in HIV-1 superinfected HeLa CD4+ cells expressing the full-length F12-HIV provirus, no infectious HIV-1 release was observed in over three months of continuous CEMss co-culture.

The inactivation of the F12 genes, alone and in all possible combinations, either by mutagenesis, e.g., insertion of a premature stop codon, or by deletion, followed by transfection of the resultant mutants into HIV-permissive human cells can be performed to determine which mutation (s) enable(s) the F12 genome to confer resistance to superinfection. Alternatively, every single mutation in the F12 genome can be reverted to wild-type and the resulting products transfected into HIV-permissive human cells. Such methods would enable the identification of the gene(s) responsible for the interference mechanism and only those genes could be mutated in other HIV genomes, thereby enabling the use of other HIV genomes in the context of the present inventive method.

Although, theoretically, any retroviral vector is suitable or can be rendered suitable for use in the present inventive method, a retroviral vector that allows expression of the F12 genome at sufficiently high levels to effect viral interference, i.e., resistance to superinfectdon, should be used. In addition, the retroviral vector should express a selective gene, preferably the gene encoding the resistance to the G418 antibiotic. Examples of retroviral vectors include N2, pLj, LXSN, and NSV. The retroviral vector that is preferred for use in the present inventive method is N2. Vectors derived from the Moloney murine leukemia virus (MoMLV) (Dr. E. Gilboa, Sloan-Kettering Institute for Cancer Research, New York, N.Y.) are especially preferred.

Measures should be taken to avoid any instability caused by the presence of two identical, repeated sequences, i.e., the 5' and 3' LTRs, in the vector. A preferred method involves deletion of the 3' LTR, which contains part of the nef gene, of the F12-HIV genome prior to insertion in the retroviral vector.

Measures should also be taken to avoid any transcriptional interference, such as that which can result between the LTRs of F12 and of the retroviral vector. A preferred measure involves insertion of the F12 genome, in particular the F12 genome from which the 3' LTR has been deleted, into the retroviral vector in antisense orientation.

In accordance with the present invention, the composition comprising a retroviral vector comprising a genome from a nondefective, nonproducer HIV variant as described above is administered directly to a human. Suitable ways of administration are known to those of ordinary skill in the art. Irrespective of which composition and method of administration are used, the recombinant retroviral vector should be administered in sufficient amount to the human to effect stable integration and expression of the nondefective, nonproducer HIV variant genome into at least some of the nuclear genomes of the cells of the human (see, e.g., Ferrari et al., Science 25: 1363 (1991); Ferrari et al., Blood 80: 1120 (1992), and Mavilio et al., Blood 83: 1988 (1994) and the protocol set forth in Borneo et al., Human Gene Therapy 4: 513 (1993)).

The retroviral vector comprising the nondefective, nonproducer HIV variant genome can be made into a composition appropriate for contacting cells in vitro, or pharmaceutical compositions appropriate for administration in vivo, with appropriate carriers or diluents, which further can be pharmaceutically acceptable. Where appropriate, the vectors can be formulated into preparations in solid, semisolid, liquid or gaseous forms, such as suppositories, injections, inhalants, and aerosols, in the usual ways for their respective way of administration. Means known in the art can be utilised to prevent release and absorption of the composition until it reaches the desired cells or to ensure timed-release of the composition. A pharmaceutically acceptable form should be employed which does not ineffectuate the composition. In pharmaceutical dosage forms, the compositions can be used alone or in appropriate association, as well as in combination, with other pharmaceutically active compounds.

The pharmaceutical compositions of the present invention can be delivered through different ways and to different sites in the body. One skilled in the art will recognise that, although more than one way can be used for administration, a particular way can provide a more immediate and more effective result than another way. Local or systemic delivery can be accomplished by administration comprising application or instillation of the composition into body cavities, inhalation or insufflation of an aerosol, or by parental introduction, comprising intramuscular, intravenous, peritoneal, subcutaneous, intradermal, as well as topical administration.

The compositions of the present invention can be provided in unit dosage form, wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the composition of the present invention, alone or in combination with other active agents, calculated-in an amount sufficient to produce the desired effect, in association with a pharmaceutically acceptable diluent, carrier, or vehicle, where appropriate. The specifications for unit dosage forms depend on the particular pharmacodynamics of the particular individual to be treated.

Accordingly, a recombinant retroviral vector comprising a nondefective, nonproducer HIV-1 variant genome can be administered to a human using any of the aforementioned ways of administration or alternative ways known to those of skill in the art and appropriate for a particular application. The amount of the vector administered should be sufficient to effect stable integration of the nondefective, nonproducer HIV variant genome into at least some of the nuclear genomes of the cells in the human and expression of the nondefective, nonproducer HIV variant genome therein. Such integration can be monitored, for example, by evidence of genome integration, e.g., using the polymerase chain reaction in conjunction with sequencing or Southern hybridizations.

The present invention composition can be used to effect intracellular immunization so as to prevent or, at the very least, substantially inhibit, initial HIV infection in an individual at risk for such an infection. It can also be used in the therapeutic treatment of an HIV+ individual by blocking or, at the very least, slowing the spread of the infection and preventing or, at the very least, delaying the onset of AIDS or ARC. In this regard, the composition can be used in combination with other antiretroviral drugs, in particular other anti-HIV treatments, provided that they do not adversely affect the ability of the nondefective, nonproducer HIV variant genome to stably integrate into at least some of the nuclear genomes of the cells in the human and to express itself therein. It should be noted that the present composition also has utility in vitro. For example, the composition could be used to study, besides further aspects concerning F12 HIV induced interference (i.e., in the SCID mouse in vivo model or in HIV chronically infected cells), the effects of HIV encoded proteins on the physiology of ex vivo cells (i.e., peripheral blood lymphocytes, monocytes, astrocytes) in the absence of viral replication.

The following Examples serve to illustrate the present invention and are not intended to limit its scope. Reference will be made to the following figures:

FIG. 1 is a schematic diagram of the sense (s) and antisense (as) nef− and nef+ N2/F12-HIV constructs described in Example 1;

FIG. 2 is a schematic diagram of the regions of the N2/F12-HIV nef− (as) genome covered by probes used in Example 4;

FIG. 3 is a schematic diagram of expected RNAs transcribed in packaging cells transfected with N2/F12-HIV nef− (S) and (as);

FIGS. 4 I, 4 II and 4 III are Southern blots of Xho I digested (a) or Eco RI digested (b) genomic DNA from infected neo$^r$ cell populations and of Eco RI digested (c) genomic DNA from nef− (as) stably transduced cell clones;

FIGS. 5*a* and 5*b* are graphs of counts full scale versus fluorescence intensity for F12-HIV nef− (as) expressing PA317 clones nos. 2 and 12, respectively;

FIGS. 6*a–d* are FACS analyses of the presence of intracytoplasmic F12-HIV gag protein in neo$^r$ CEMss cells after cocultivation with either PA317 clone no. 2 (FIG. 6*c*) or PA317 clone no. 12 (FIG. 6*d*). Uninfected CEMss cells (FIG. 6*a*) and HUT-78/F12 cells (FIG. 6*b*) served as negative and positive controls, respectively. Also shown in the figures are percentages of positive cells;

FIGS. 7*a* and 7*b* are Southern blots of restriction enzyme-digested genomic DNA of neo$^r$ CEMss cells transduced by cocultivation with "producer" PA317 clone no. 2 or no. 12 and hybridized with F12-HIV genomic and neo probes, respectively;

FIG. 8 is a Southern blot of Hind III digested genomic DNA from neo$^r$ CEMss and HUT-78 cells transduced by cocultivation with "producer" PA317 clone no. 2 or no. 12 and hybridized with the neo probe.

FIGS. 9*a–d* are Northern blots of polyA+ RNA from F12 cells (lane 1), parental CEMss cells (lane 2), and N2/F12-HIV nef− (as) transduced CEMss clone 40 (lane 3) hybridized with full-length F12-HIV (FIG. 9*a*), F12-HIV U3 LTR (FIG. 9*b*), F12-HIV nef (FIG. 9*c*), and F12-HIV env probes (FIG. 9*d*), i.e., F12-HIV-specific probes;

FIG. 10*a–d* are Northern blots of polyA+ RNA from F12 cells (lane 1), CEMss cells transduced with a double-promoter retroviral vector pLj (lane 2, Korman et al., PNAS USA 84: 2150–2154 (1987)), and N2/F12-HIV nef− (as) transduced CEMss clone 40 (lane 3) hybridized with neo (FIG. 10*a*), U3-MLV (FIG. 10*b*), R/U5-MLV (FIG.10*c*), and MLV (FIG. 10*d*) N2-specific probes;

FIG. 11 is the result of a RIPA assay with representative N2/F12-HIV nef− (as) transduced CEMss clones performed with either a mixture of HIV+ or HIV-sera;

FIGS. 12*a–c* are graphs of counts full scale versus fluorescence intensity representing FACS analysis of anti-gag HIV treated HUT78-F12 cells (FIG. 12*a*, positive control), uninfected PBLs (FIG. 12*b*, negative control), and fresh human PBLs 5 days after termination of cocultivation with PA317 clone no. 12 (FIG. 12*c*);

FIG. 13 is a graph of cpm/ml of culture supernatant x 10-3 versus days postinfection (p.i.);

FIG. 13*a* is a graph of % of cell viability versus days p.i. for representative N2/F12-HIV nef− (as) CEMss transduced clones, i.e., 15, 40 and 41, superinfected with $5\times10^3$ $TCID_{50}$/$10^6$ cells;

FIG. 14 is a graph of cpm/ml of culture supernatant versus days postinfection (p.i.);

FIG. 14*a* is a graph of % of cell viability versus days p.i. for representative N2/F12-HIV nef− (as) CEMss transduced clones, i.e., 15, 40 and 41, superinfected with $10^5$ $TCID_{50}$/$10^6$ cells.

All enzymes were used according to manufacturers' recommendations. The *E. coli* XL-1 Blue strain was used to amplify the pUC-based plasmids, whereas the *E. coli* JM 109 strain was used to amplify the pBR-based plasmids. Bacterial transformations were performed in accordance with Bio-Rad's protocols (Richmond, Calif.) for electroporation. Titres of the amphotropic retrovirus preparations were assayed as colony forming units (cfu)/ml on NIH 3T3 cells as previously described (Federico et al., J. Gen. Virol. 74: 2099–2110 (1993)). HTLV-III$_B$ and NL4-3 strains of HIV were obtained from the supernatants of acutely infected CEMss cells. HIV titers, which ranged from 1–3×10$^6$ TCID$_{50}$/ml, were measured by scoring the number of syncytia formed on C8166 cells 5 days after infection with serially diluted virus preparations as described by Federico et al. (1995), supra. HIV release after superinfection was monitored by reverse transcriptase (RT) assay (Rossi et al., Ann. NY Acad. Sci. 511: 390–400 (1987)).

EXAMPLE 1

Construction of Sense and Antisense N2/F12-HIV nef− and N2/F12-HIV nef+ Retroviral Vector Constructs.

The full-length F12-HIV proviral DNA was cloned from a HUT-78/F12 cell genomic library as previously described (Carlini et al., J. Viral Diseases 1: 40–55 (1992)). The N2 retroviral vector was provided by E. Gilboa (Keller et al., Nature 318: 149 (1985)). Four different N2/F12-HIV constructs were obtained as shown in FIG. 1. FIG. 1 is a schematic diagram of the sense (s) and antisense (as) nef− and nef+ N2/F12-HIV constructs, including the relative positions of the 5' and 3' long terminal repeats, 5' LTR and 3' LTR respectively, restriction enzyme sites, neomycin resistance marker gene (neo), and the position of the nucleotide sequence AACCAA (SEQ ID NO: 1) within the 5' LTR. The symbol "//" is used to indicate that the construct maps presented are shortened for purposes of illustrating the regions of interest. N2/F12-HIV nef− represents the constructs wherein the F12-HIV genome was inserted into the Xho I site of N2 in the same, i.e., "sense" or (s), or opposite, i.e., "antisense" or (as), transcriptional orientation, after removal of part of the nef gene. N2/F12-HIV nef+ represents the constructs wherein the F12-HIV genome was inserted into the Xho I site of N2 in the same or opposite transcriptional orientation after removal of part of the 3' LTR and the negative regulatory elements (NRE) of the 5'LTR.

In order to avoid premature polyadenylation of RNA transcribed from the N2 5' LTR in the sense constructs, the AATAAA (SEQ ID NO: 2) consensus of the F12HIV 5' LTR was mutagenized to AACCAA (SEQ ID NO: 1). The mutagenesis was performed utilizing a degenerated oligoprimer (5'GGCAAGC<u>TTGGTT</u>GAGGCTTAAGCAGT 3', SEQ ID NO: 3), which encompassed both the consensus AATAAA (SEQ ID NO: 2) and the adjacent Hind III restriction site, in "reverse" orientation and a second primer overlapping the Sma I site in the opposite strand of the 5' LTR U3 region (5'ATGGATGACCCGGGGAGAAGAGAAAA 3', SEQ ID NO: 4). A DNA PCR was performed to amplify 1 ng of pUC19 into which the F12-HIV 5' LTR was subcloned. The DNA PCR product was digested with Sma I/Hind III and inserted into a pUCl9/F12-HIV 5' LTR plasmid lacking both the Hind III site of the pUC polylinker, through ligation of a Hind III/Hind II-digested pUC10 plasmid after conversion of the 5' Hind III protruding ends and reinsertion of the 5' F12-HIV LTR, and the Sma I/Hind III part of the nonmutated 5' LTR. The success of the mutagenesis was checked by Sanger sequencing (Sequenase kit, UBS, Cleveland, Ohio.).

The N2/F12-HIV nef− constructs were obtained by digesting the whole F12-HIV provirus (Carlini et al., supra) with Tha I, which recognizes a single site in the leader sequences of F12-HIV, and Sma I, which cleaves the U3 region of both LTRS. The Tha I/Sma I digested F12-HIV genome was then ligated with the mutagenized pUCl9/F12 HIV 5'LTR, which was previously digested with Kpn I, blunt-ended with T4 DNA polymerase (BBR, Mannheim, Germany) and dephosphorylated. An Xho I site was added at the unique Xba I site (nt 1) of the F12-HIV genome in order to allow insertion of the F12-HIV genome into the Xho I cloning site of N2. Then, after digestion with Xho I, the DNA fragment encompassing the F12-HIV genome from nt 1 to nt 8930 was inserted into the Xho I site of the N2 vector and both the sense and antisense constructs were recovered.

The N2/F12-HIV nef+ constructs were obtained by digesting the pUC polylinker region of the mutagenized F12-HIV 5'LTR, which was subcloned as described (Carlini et al., supra), with Ava I, which cleaves the 5' LTR at nts. 232 and 295, and Eco RI, to generate an Ava I-Eco RI fragment for reinsertion into an Ava I-Eco RI digested pUC19 vector. Accordingly, the resulting 5'LTR lacked nts 1–295 of the U3 region, which corresponds to most of the negative regulatory elements (NRE) (Lu et al., J. Virol. 64: 5226–5229 (1990)). The 5'LTR construct was then digested with Xba I and Kpn I, blunt-ended at the Kpn I end, and inserted into a Xba I-Bss HII digested pUC19 (Sac I-Sac I) F12-HIV genome (Carlini et al., supra), which was blunt-ended at the Bss HII end (Bss HII and Tha I recognize unique, adjacent sites in the leader sequence). Not I sites were created adjacent to the Xba I (nt 1) and Aat II (570 nts downstream to the Sac I truncated F12-HIV 3'LTR in the pUC 19 vector) sites to allow insertion of the F12-HIV nef+ genome into the N2 vector. An additional Not I site was then added at the N2 cloning site. Not I-Not I ligation of N2 with the modified (as described above) F12-HIV genome generated both the sense and antisense nef+ constructs.

EXAMPLE 2

Cell Culture and Transfection Methods

CEMss, HUT-78, H9/HTLV$_{IIIB}$ and C8166 cells were maintained in RPMI 1640 medium supplemented with 10% fetal calf serum (FCS). HeLa, NIH 3T3, GP+E86 (Markowitz et al., J. Virol. 62: 1120–1124 (1988)), and PA317 (Miller et al., Mol. Cell. Biol. 6: 2895–2902 (1986)) cells were maintained in Dulbecco's modified minimal essential medium (MEM) supplemented with 10% FCS. CEMss and HUT-78 cells were grown in the presence of 1 mg/ml G418 (GIBCO BRL, Gaithersburg, M D. 50% of activity) for selection, whereas both packaging and NIH 3T3 cells were grown in the presence of 0.5 mg/ml G418, with selection being started 48 hrs after infection cycles.

Cell cloning was performed by seeding 96-well plates with 0.5 cells/well in accordance with the limiting-dilution method (Federico et al. (1995), supra). Human peripheral blood lymphocytes (PBLs), which were obtained as described previously (Rossi et al., supra), were stimulated with phytohemagglutinin (PHA) for 48 hrs and then were cultivated in RPMI 1640 supplemented with 20% FCS and 50 U/ml recombinant human IL-2 (rhIL-2, Roche, Nutley, N.J.).

Cell monolayers were transfected by the calcium-phosphate precipitation method (Wigler et al., Cell 16: 758–777 (1979)). Briefly, 10 g of plasmid DNA were precipitated and added to subconfluent cultures in 10 cm diameter dishes. Four hours later, the precipitate was removed and the cells were washed and supplied with fresh complete medium. Two days later, supernatants were removed and used as a source of retrovirus.

Transient transfection experiments were performed on HeLa, NIH 3T3 and PA317 cells utilizing each of the four different N2/F12-HIV constructs and the intracellular presence of the F12-HIV gag proteins on cells (105) was assessed two days later. Cell transfection with the N2 vector alone was used as a negative control. The results are shown in Table I, which provides the intracytoplasmic F12-HIV gag protein amounts (pg p24 HIV protein/$10^5$ cells) in N2/F12-HIV-transfected cells 48 hrs post-transfection and after G418 selection.

TABLE I

Intracytoplasmic F12-HIV gag protein amounts* in N2/F12-HIV-transfected cells

| Retroviral Construct | 48 hours post-transfection | | | after G418 selection | |
|---|---|---|---|---|---|
| | HeLa** | NIH 3T3 | PA317 | HeLa | NIH 3T3 |
| N2 | <20 | <10 | <10 | <10 | <10 |
| N2/F12-HIV nef− (s) | 124.3 + 10.8 | 37.3 | 63.5 | >246 | 184.5 |
| N2/F12-HIV nef− (s) | 239.2 + 20 | 25.7 | 121.1 | >246 | 130.6 |
| N2/F12-HIV nef+ (s) | 160.2 + 18.3 | 40 | 44.7 | >246 | 211.5 |
| N2/F12-HIV nef+ (s) | 203.1 + 1.2 | 11.2 | 117.5 | 210 | 90.5 |
| pUC/F12-HIV | 134.5 + 10 | 88.4 | 67.4 | >246 | ND |

*picograms of p24 HIV protein in $10^5$ cells
**average of four independent experiments ± s.d.

The results show that the modifications performed on the F12-HIV genome did not adversely affect the expression of the genome. In fact, no significant differences in the production of gag proteins were observed among the four retroviral constructs compared to the full-length F12-HIV genome inserted into the pUC 10 plasmid (Carlini et al., supra). Significantly higher amounts of gag proteins were observed in human cells compared to mouse cells, both 48 hrs post-transfection and after G418 selection, probably due to the stronger activity of the HIV promoter in humans compared to mice (Trono et al, EMBO 9: 4155–4160 (1990)). Similar results were obtained in stable transfected HeLa and NIH 3T3 cells, although the amounts of gag proteins were higher compared to the amounts observed in the transiently transfected cells (see Table I).

EXAMPLE 3

Retroviral Constructs are able to Generate Recombinant Retroviral Particles

Supernatants from transfected GP+E86 and PA317 cells were used to infect subconfluent monolayers of PA317 (single cycle of infection) or CEMss (four cycles of infection) cells, respectively, which were pretreated with 8 mg/ml polybrene (Sygma, St. Louis, Mo.). Cocultivations were performed in order to infect either CEMss cells or human PBLs with the amphotropic retrovirus released by PA317 producer cell clones. Producer cells ($10^5$) were seeded in 1 ml cultures with either CEMss cells ($10^5$) or PBLs ($_{10}{}^6$). After 24 hrs, PA317 cells were removed and, in order to completely eliminate the producer cells, the culture plates were changed every 24 hrs for CEMss or every 12 hrs for PBLs. G418-resistant (neo$^r$) PA317 cells were recovered after infection with the supernatant from transfected, ecotropic GP+E86 cells. In addition, F12-HIV expressing neor human CEMss cells resulted from infection with supernatant from transfected, amphotropic PA317 cells.

EXAMPLE 4

Analysis of DNA, RNA and Proteins of the Infected Cells

Figure 2:
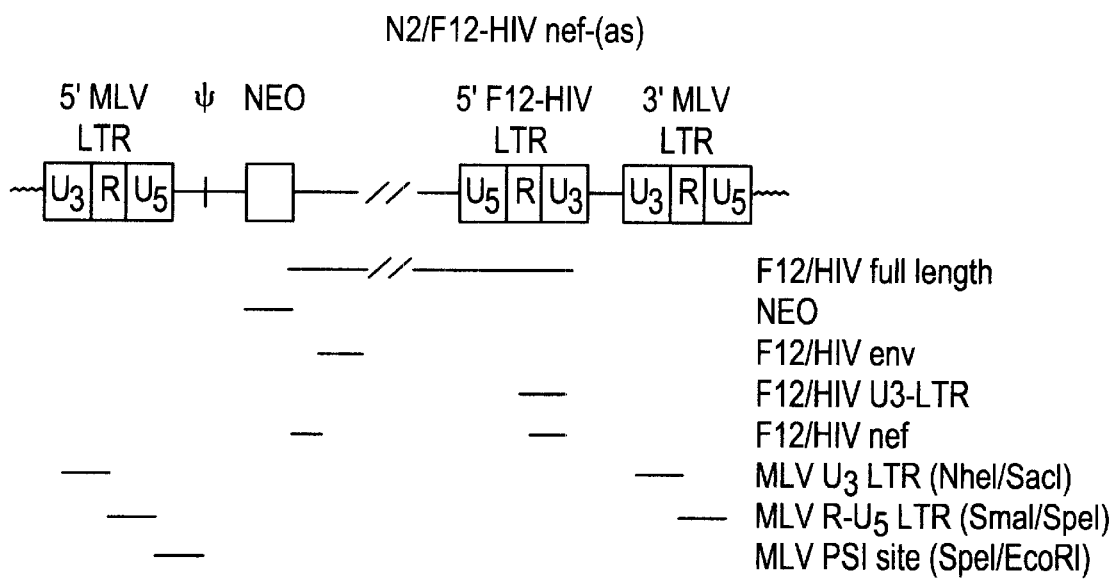

Genomic DNA was prepared by standard methods (Maniatis et al., *Molecular Cloning: A laboratory manual*, Nolon, C., ed., Cold Spring Harbor Laboratory, Cold Spring Harbor, N.Y. (1989)). Total RNA was extracted by the guanidine-isothiocyanate method (Chirgwin et al., Biochemistry 18: 5294 (1979)) and the poly A+ fraction was obtained through separation with oligo-dT coupled dynabeads (Dynal, Oslo, Norway). Southern and Northern blots were performed as described (Maniatis et al., supra). Probes were radioactively labelled with $^{32}$P at a specific activity of 0.5–2×$10^9$ cpm/μg DNA using the random primer method and are shown in FIG. 2, which is a schematic diagram of the regions of the N2/F12-HIV nef− (as) genome covered by the probes. The F12-HIV genomic probe was obtained by excising the provirus from the N2/F12-HIV nef− constructs. The full-length Tn5 bacterial transposon was used as the neo probe. F12-HIV env and nef DNAs were obtained after cloning DNA-PCR amplification products into the Eco RI site of pUCl9 using Eco RI tailed oligo-primers overlapping the start and stop codons of each gene. The F12-HIV U3 LTR probe was recovered by Xba I-Sma I digestion of the F12-HIV 5'LTR cloned in the pUC19. The N2-specific probes were recovered after N2 digestion with Nhe I and Sac I for the LTR-U3 probe, Sma I and Spe I for the LTR-R/U5 probe, and Eco RI and Spe I for the N2 (packaging site) site-specific probe (see FIG. 2).

Figure 4A:
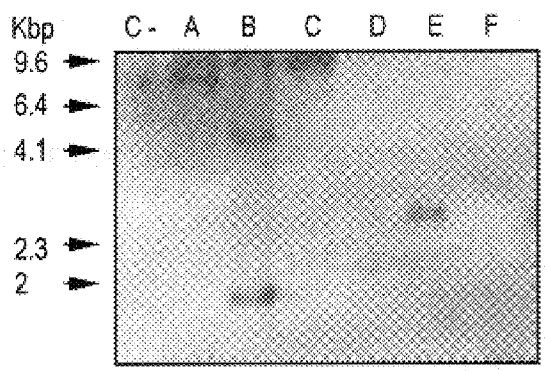
Figure 4B:
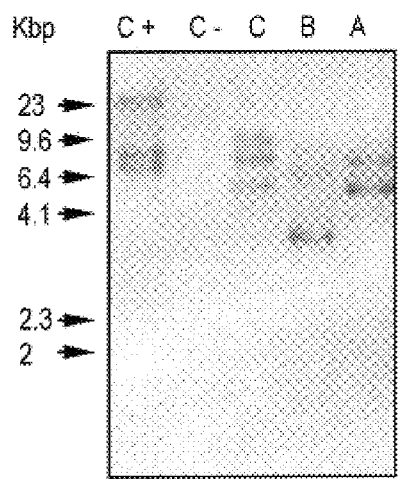
Figure 4C:
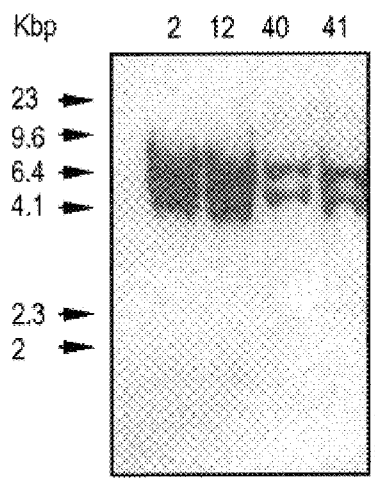

FIGS. 4I-III are Southern blots of Xho I-digested (a) or Eco RI-digested (b) genomic DNA from infected neo$^r$ cell populations and of Eco RI-digested (c) genomic DNA from nef− (as) stably transduced cell clones. In FIGS. 4I and 4II, DNA from neo$^-$ nef− (as) and nef− (s) transduced CEMss cells are shown in lanes A and B, respectively, whereas DNA from neo$^r$ nef− (as), nef− (s), nef+ (as) and nef+ (s) infected PA317 cells are shown in lanes C-F, respectively. In FIG. 4III, DNA from nef− (as) PA317 (2 and 12) and CEMss (40 and 41) cell clones are shown. DNA from uninfected CEMss (C−) and from H9-HTLV$_{IIIB}$ cells (C+) were used as negative and positive controls, respectively. Hind III-digested phage DNA was used as a molecular marker (on left).

The Southern blot of the Xho I-digested DNA from neo$^r$ CEMss cells infected with the supernatant from N2/F12-HIV nef− (as) transfected PA317 cells showed a 9 kb band (FIG. 4I, lane A), as expected, since the entire F12-HIV genome is excised from the construct by Xho I digestion, plus an additional signal at a lower molecular weight, probably derived from a genomic rearrangement. In contrast, no extra bands were detected in the Xho I DNA pattern of neo$^r$ PA317 cells infected with the supernatants from nef− (as) transfected GP+E86 cells (FIG. 4II, lane A), whereas an unexpected signal was detectable in PA317 cells (FIG. 4II, lane C).

Figure 3:
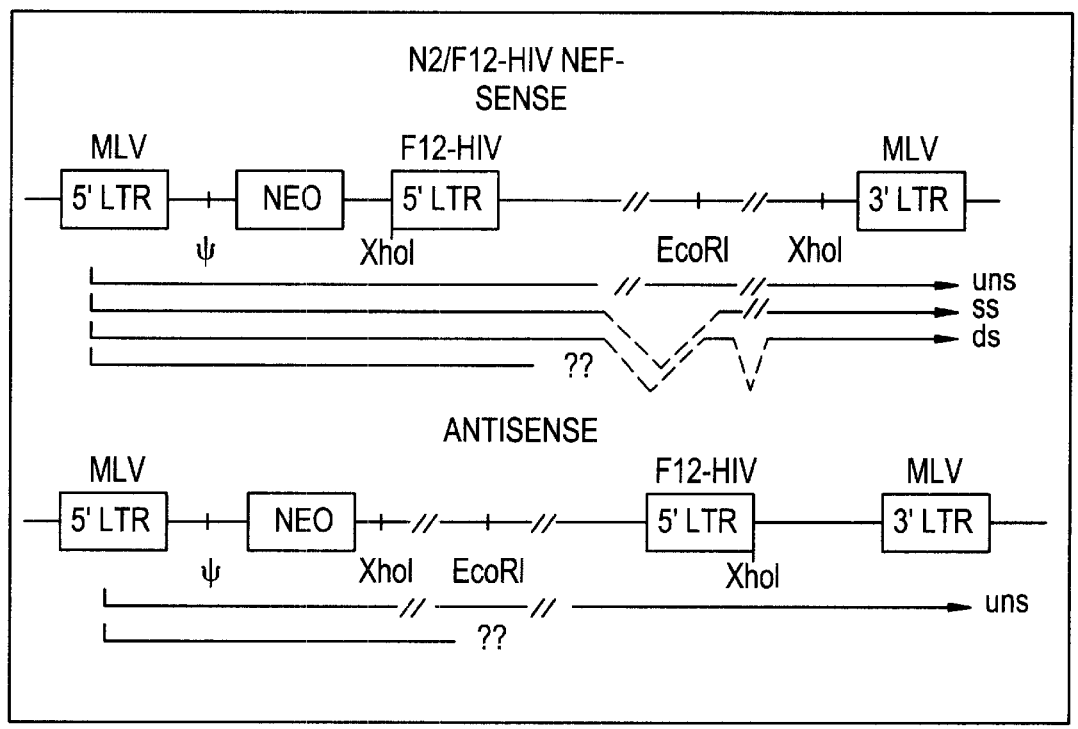

Southern blot of the Xho I-digested DNA from neo$^r$ CEMss cells infected with the supernatant of PA317 cells transfected with the supernatants from N2/F12-HIV nef− (s) (FIG. 4I, lane B) demonstrated the integration of three different F12-HIV specific DNAs, most likely originating from the three major forms of the F12-HIV RNA (i.e. unspliced, single and double spliced forms as shown in FIG. 3, which is a schematic diagram of the expected RNAs transcribed in packaging cells transfected with N2/F12-HIV nef− (s) and (as)) (Federico et al. (1989), supra). These data were also confirmed by Eco RI digestion (FIG. 4II, lane B).

Conversely, no F12-HIV-specific signals were detectable in genomic DNA from neo$^r$ PA317 cells infected with the supernatant from transfected nef– (s) GP+E86 cells (FIG. 4I, lane D), indicating a very low efficiency of transduction of an F12-HIV sequence in these cells.

Attempts to recover CEMss cells after infection with nef+ transfected PA317 supernatants and G418 selection were unsuccessful. Southern blot analysis of Xho I digested DNA from neo$^r$ PA317 cells revealed the presence of a single band in the PA317 cells infected by the nef+ (s) retrovirions (FIG. 4I, lane E). The molecular weight of this signal (about 3 kb) indicates that only double-spliced F12-HIV RNA molecules were packaged in the infectious recombinant retrovirions. Conversely, no band was detected in the PA317 cells infected with the nef+(as) retrovirions (FIG. 4I, lane F).

In order to assess the functionality of the N2/F12-HIV constructs transduced into the cells by retroviral infection, all neo$^r$ cell populations were tested for intracytoplasmic accumulation of the F12-HIV-encoded gag proteins. Intracellular p24 antigen in retroviral infected cells was determined by lysing cells ($10^5$) in 200 μl of TNE (Tris-HCl 10 mM, NaCl 100 mM, EDTA 1 mM, pH 7.4) buffer containing 0.1% Triton X-100 (Sygma, St. Louis, Mo.). After 5 min of incubation on ice, cell lysates were centrifuged briefly and the resulting supernatants were tested by ELISA-antigen capture assay (Abbott, North Chicago, Ill.).

Figure 11:
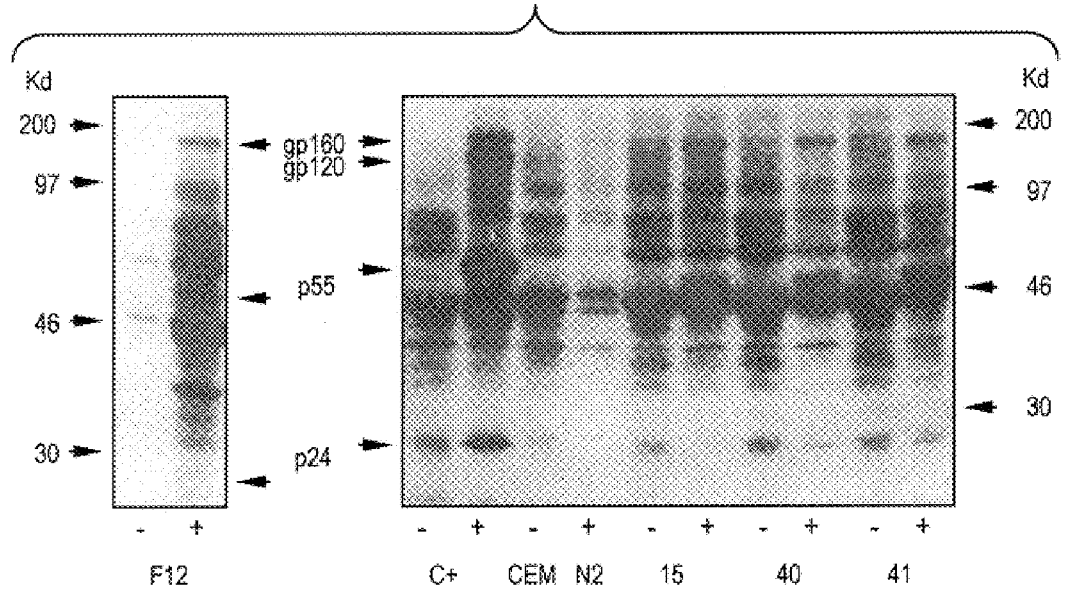

HIV-related proteins were detected by radioimmunoprecipitation assay (RIPA, Federico et al. (1995), supra). The results of RIPA assay of representative N2/F12HIV nef– (as) transduced CEMss clones performed with either a mixture of HIV+ or HIV– serum are shown in FIG. 11. Lysates from F12 and H9/HTLV$_{IIIB}$ cells were used as positive controls, whereas lysates from N2 transduced CEMss cells were utilized as a negative control. $^{14}$C-labelled molecular markers and HIV proteins detectable in RIPA are also marked.

In view of the above results, only nef–expressing cells were analyzed by ELISA assay. The results are presented in Table II, which provides the intracytoplasmic F12HIV gag protein amounts (expressed in picograms of gag protein in $10^5$ neo$^r$ cell populations; average values of 4 different experiments S.D.) for neo$^r$ cells infected with sense (s) or antisense (as) N2/F12-HIV recombinant retroviruses and the number of F12-HIV-expressing cell clones out of the total cell clones scored.

TABLE II

| neo$^r$ Cell Line | Amount of Intracytoplasmic F12-HIV gag protein* | | Number of F12-HIV Expressing Cell Clones | |
|---|---|---|---|---|
| | N2/F12-HIV (s)** | N2/F12-HIV (as) | N2/F12-HIV (s) | N2/F12-HIV (as)** |
| PA317 | <10 | 23.3 ± 2.4 | 0/14 | 11/92 |
| CEMss | 11 ± 1.2 | 106.3 ± 7 | 0/140 | 6/26 |

*picograms of gag protein in $10^5$ cells
**average of four independent experiments + s.d.

The results show that no intracytoplasmic F12-HIV gag protein was detected in the neo$^r$ PA317 cells infected by the nef– (s) virions. Although low levels of intracytoplasmic protein were initially detected in the neo$^r$ CEMss cells infected by the nef– (s) amphotropic retrovirus, no intracytoplasmic protein was detected with cell passages.

In contrast, higher levels of F12-HIV gag proteins were detectable in both PA317 and CEMss cells integrating the nef– (as) genome. These positive values remained stable over a long period of time, i.e., over 1 yr.

In order to evaluate the percentage of cells stably expressing the F12-HIV genome, the neo$^r$ PA317 and CEMss cells integrating the nef– genome in either the (s) or (as) orientation were cloned by the limiting dilution method. As shown in Table II, no F12-HIV expressing nef– (s) clones were isolated from either PA317 or CEMss neo$^r$ cells, even if the latter were initially positive in the ELISA test. In contrast, PA317 cell clones expressing the nef– (as) genome were readily available (about 12%); moreover, about 23% of CEMss clones were able to synthesize the gag proteins.

EXAMPLE 5

Fluorescence-activated Cell Sorting (FACS) Analysis of the Infected Cells

CD4 receptors on the plasma membrane were detected by indirect immunofluorescence and analyzed by a cytofluorimeter as described by Taddeo et al. (Virology 194: 441–452 (1993)). Briefly, cells ($10^6$) were incubated with the appropriate concentration of an anti-CD4 monoclonal antibody (mAb, Ortho Diagnostic, Raritan, N.J.) in 100 μl of phosphate-buffered saline (PBS) containing 2.5% FCS. After 1 hr of incubation on ice, the samples were washed twice in PBS and further incubated for 1 hr on ice with 100 μl of 1:20 goat anti-mouse IgG conjugated with fluoresceine isothiocyanate (Ortho Diagnostic, Raritan, N.J.). After three washes with PBS, samples were fixed with a 2% v/v solution of formaldehyde and analyzed by a cytofluorimeter (FAC-scan, Becton-Ditkinson, Mountain View, Calif.).

Intracytoplasmic HIV gag-related proteins were detected by direct immunofluorescence. Cells ($10^6$) were washed three times with PBS buffer complemented with 2.5% FCS and resuspended in 200 μl PBS-EDTA (10 mM). A solution of PBS-formaldehyde (2% v/v) was then added and the cells were incubated at room temperature (RT) for 10 min. After two washings with the PBS/FCS buffer, the cells were resuspended in 40 μl of cold PBS-EDTA. Then, 400 μl of cold methanol were added dropwise and the cells were incubated on ice for an additional 10 min. Cells were then washed three times and incubated for 1 hr at RT with a 1:50 dilution of KC57-RD1 (Coulter Corp., Hialcam, Fla.) anti-gag HIV mAb coupled with phycoerythrin (PE). Finally, the cells were washed three times with PBS-FCS buffer and analyzed by a cytofluorimeter. Both uninfected cells and PE-conjugate nonspecific mouse IgG1 antibodies (Coulter Corp.) were used as negative controls.

Supernatants from 11 F12-HIV nef– (as) expressing PA317 clones were titrated as cfu/ml on NIH 3T3 cells. Retroviral titers were relatively low, ranging between 4.6× $10^2$ to 4×$10^4$ cfu/ml, as expected, given the large size of the retroviral construct, i.e., approx. 11 kb.

Figure 5A:
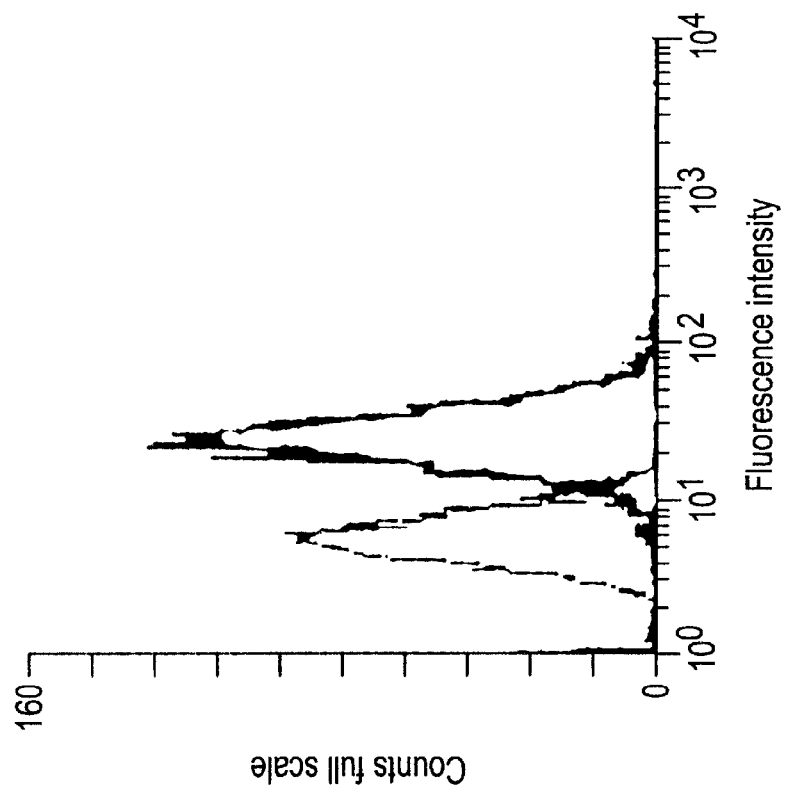
Figure 5B:
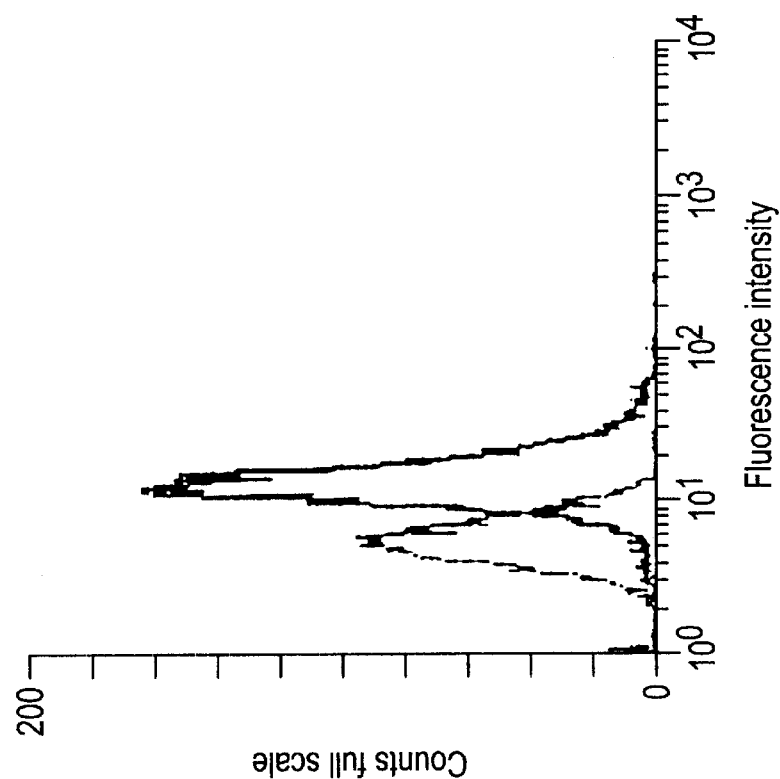

DNA analysis of the two PA317 clones (nos. 2 and 12) producing the highest retroviral titers indicated that the retroviral construct was fully integrated into the host genome (FIG. 4III) and was efficiently transcribed as demonstrated by Northern blot analysis. Intracytoplasmic direct immunofluorescence of the F12-HIV specific gag proteins is shown in FIGS. 5a and 5b, which are graphs of counts full scale versus fluorescence intensity for F12-HIV nef– (as) expressing PA317 clones nos. 2 and 12, respectively. In both graphs, the slope of anti-gag HIV-treated PA317 cells is reported as a negative control. As shown in FIG. 5, both clones were able to homogeneously express the F12-HIV genome.

EXAMPLE 6

Molecular Characterization of Transduced CEMss Cells and Human PBLs

Figure 6D:
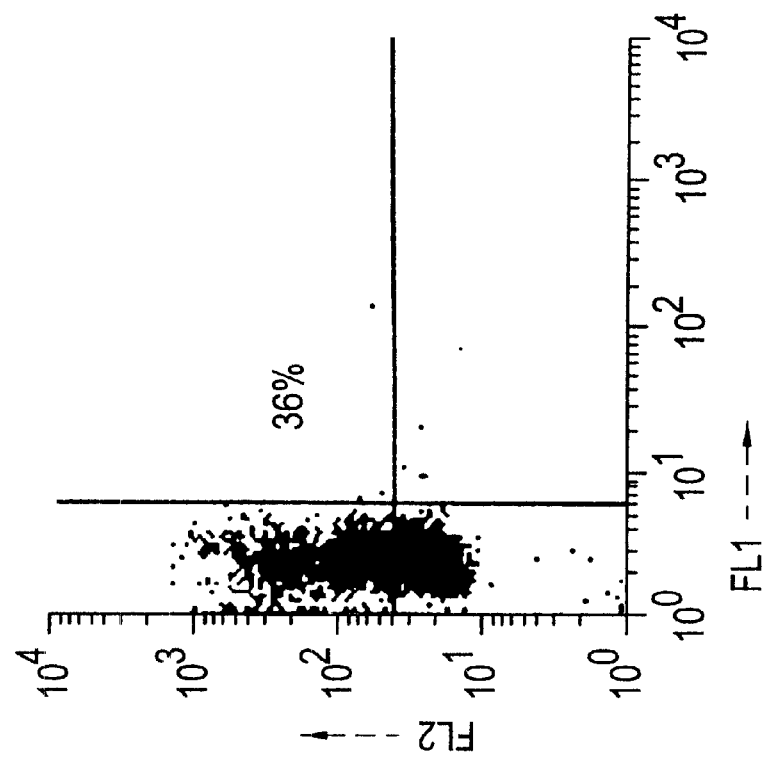
Figure 6C:
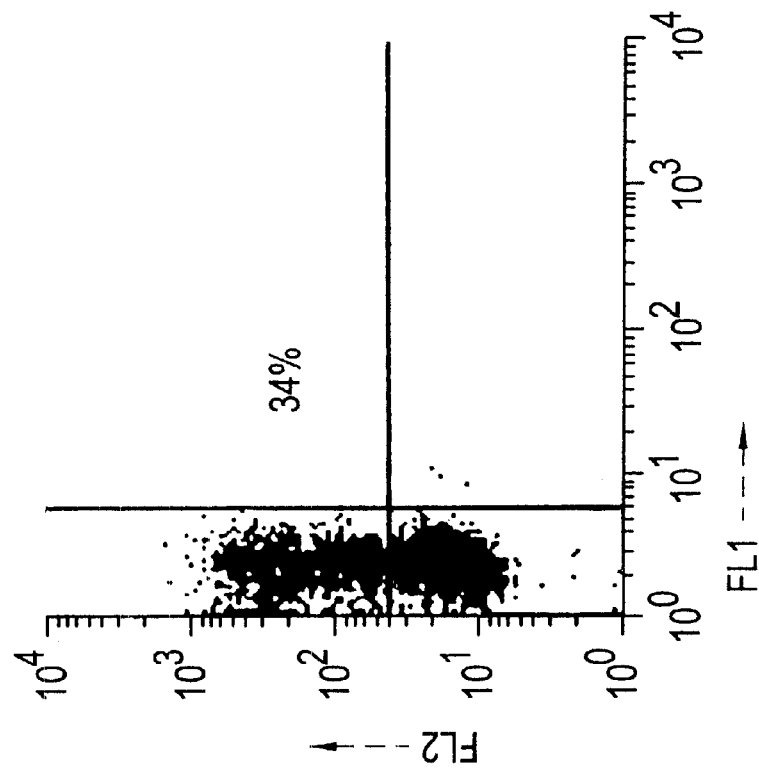

PA317 clones were cocultivated with CEMss cells and PHA-stimulated fresh human PBLs in order to transduce the F12-HIV genome into HIV-susceptible cells. Twenty four hrs after the cocultivations, G418 was added to CEMss cells and a neo$^r$ cell population was obtained 20 days later. The percentage of neo$^r$ cells expressing intracytoplasmic F12-HIV ,ga,e protein was assayed by FACS analysis. The results are shown in FIGS. 6a–d, which represent the FACS analyses of the presence of intracytoplasmic F12-HIV gag protein in uninfected CEMss cells (negative control, FIG. 6a), HUT-78/F12 cells (positive control, FIG. 6b), neo$^r$ CEMss cells after cocultivation with PA317 clone no. 2 (FIG. 6c), and neo$^r$ CEMss cells after cocultivation with PA317 clone no. 12 (FIG. 6d). Also shown are the percentages of positive cells for each. As shown in FIG. 6a–d, about 35% of neo$^r$ cells expressed the F12-HIV genome. These data were replicated in HUT-78 cells. Moreover, 36/60 CEMss cell clones scored, i.e., 55%, expressed the F12-HIV genome as assessed by the HIV gag-specific ELISA.

Figure 7A:
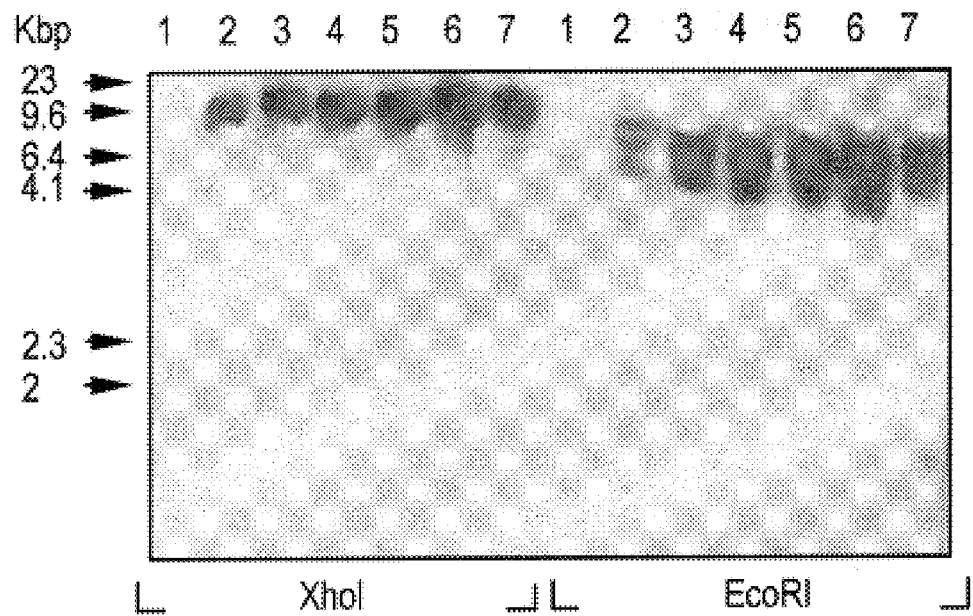
Figure 7B:
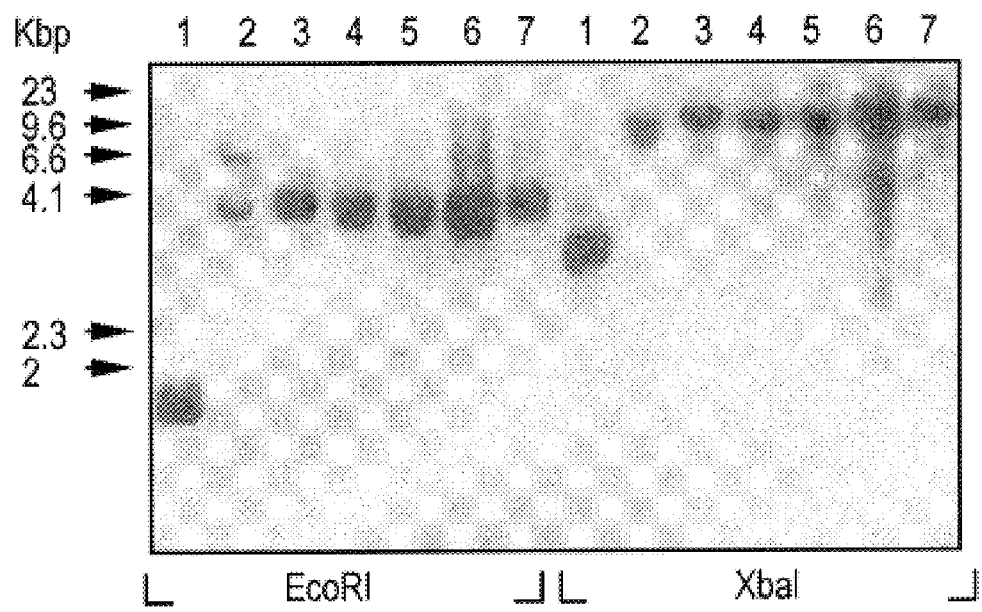

Southern blots of restriction enzyme-digested genomic DNA of neo$^r$ CEMss cells transduced by cocultivation with "producer" PA317 clone no. 2 or 12 was hybridized with F12-HIV or neo specific probes as shown in FIGS. 7a and 7b, respectively. Lane 1 represents DNA from N2 transduced CEMss cells, whereas lane 2 represents DNA from neo$^r$ CEMss cells transduced by uncloned N2/F12-HIV nef– (as) PA317 cells, lanes 3 and 4 represent neo$^r$ CEMss cells after cocultivation with PA317 clone no. 2 or clone no. 12, respectively, lanes 5 and 6 represent neo$^r$ HUT-78 cells after cocultivation with either PA317 clone no. 2 or clone no. 12, respectively, and lane 7 represents PA317 clone no. 12. The genomic DNA was digested with the restriction enzyme indicated and the DNA molecular marker was the same as that in FIGS. 4I–III. The hybridizations indicate that the F12-HIV genome fully integrated without apparent genomic rearrangements.

Figure 8:
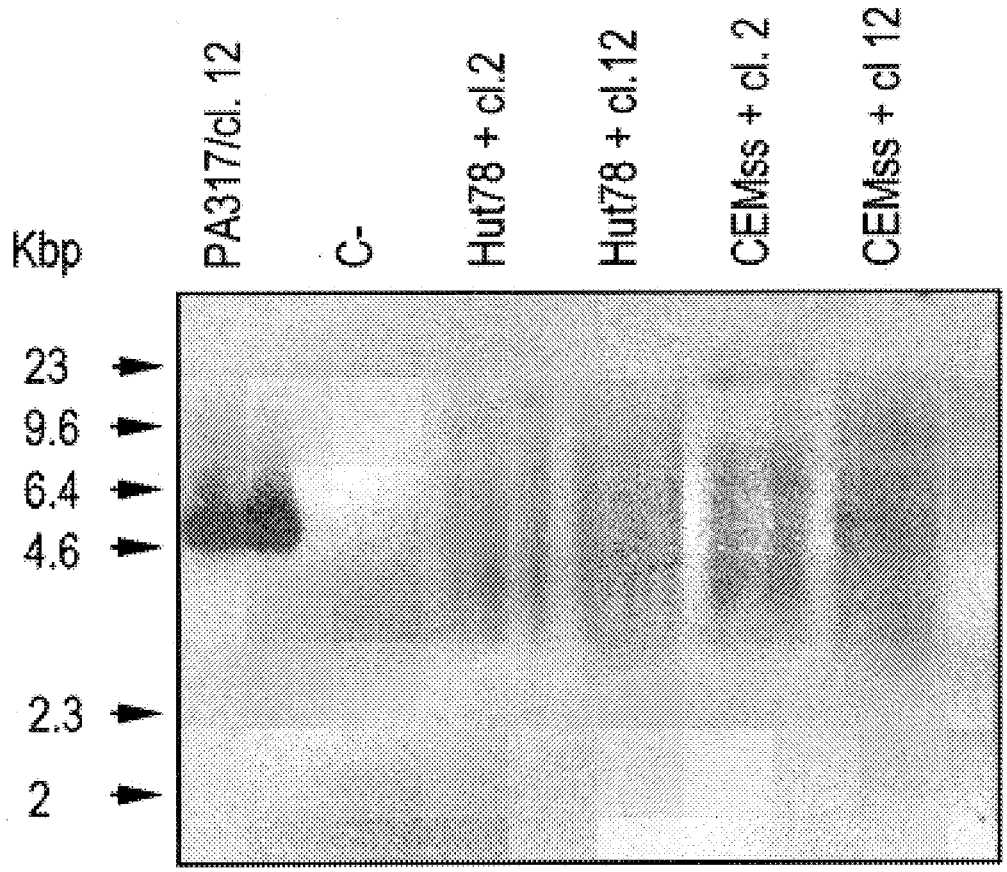
Figure 9A:
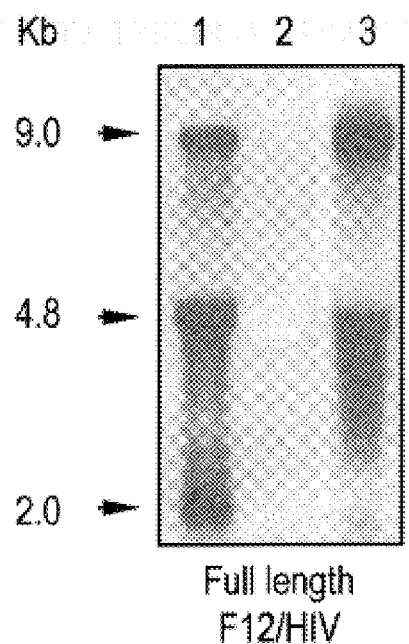
Figure 9B:
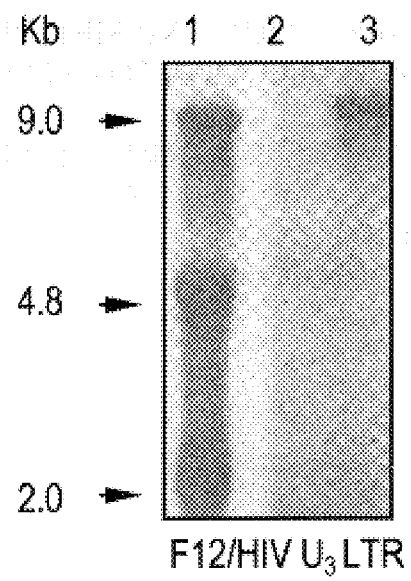
Figure 9C:
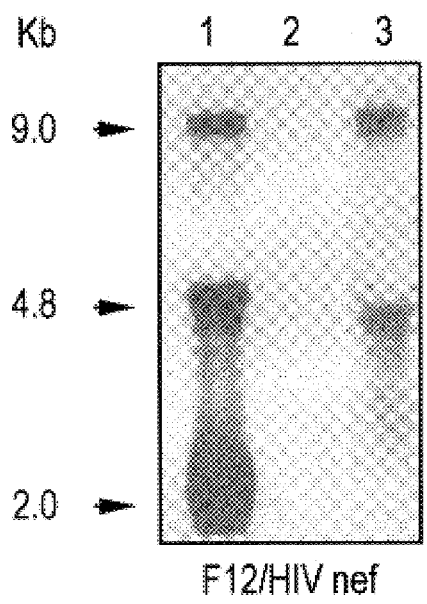
Figure 9D:
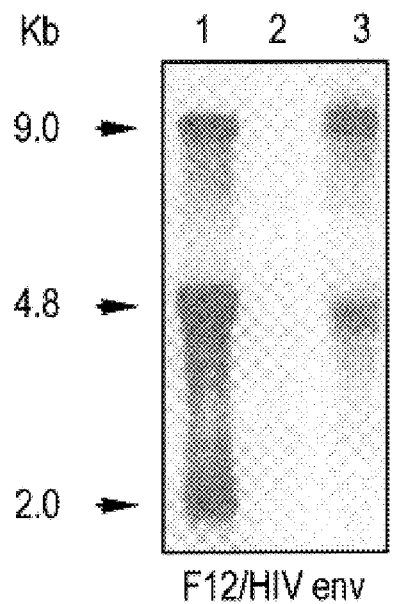
Figure 10A:
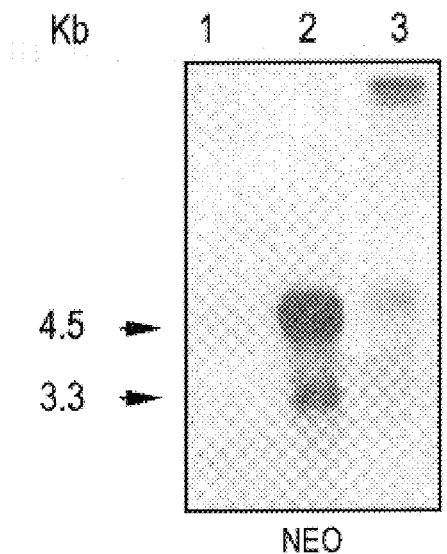
Figure 10B:
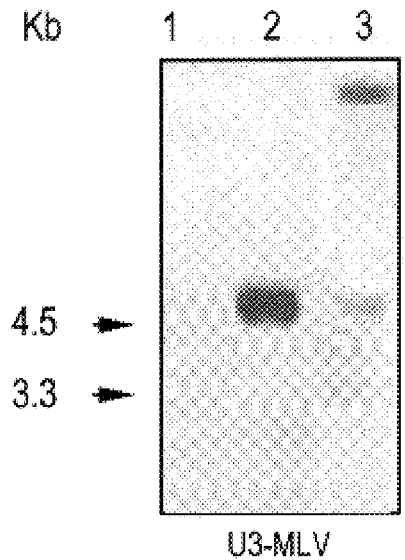
Figure 10C:
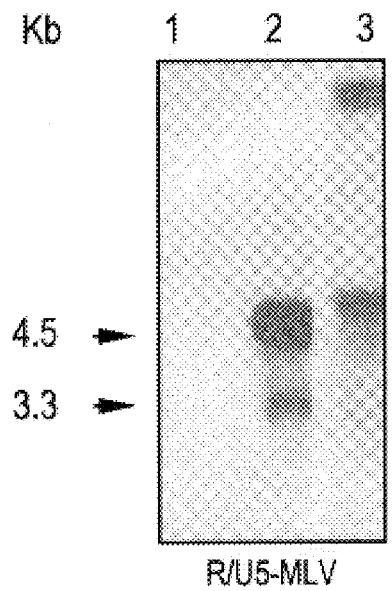
Figure 10D:
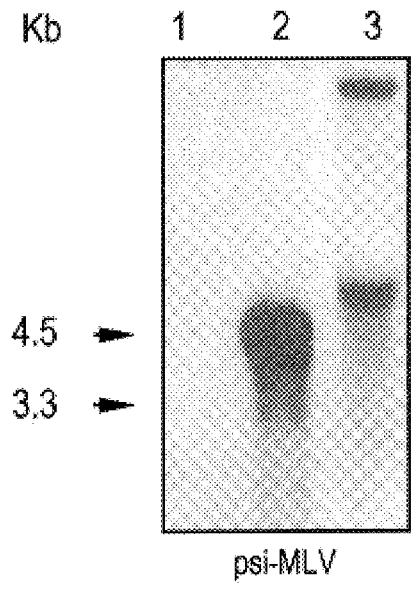

In order to estimate the frequency of the infection events in CEMss cells, the clonality of the neo$^r$ cells was examined. Hind III-digested genomic DNA of neo$^r$ CEMss or HUT-78 cells transduced by cocultivation with "producer" PA317 clone no. 2 or 12 was hybridized with the neo probe as shown in FIG. 8, which is a Southern blot of such hybridizations. Starting from the N2 5' LTR side of the N2/F12HIV nef– (as) construct, the first site recognized by the Hind III enzyme resides in the F12 env gene, about 3 kb from the N2 5' LTR end. As controls, DNA from PA317 clone no. 12 (positive) and parental CEMss cells (negative) were utilized. The molecular weight marker was the same as that in FIGS. 4I–III. Hybridization of the genomic DNA with the neo probe demonstrates that the T-cell transduced cultures were largely polyclonal, thus excluding the possibility that the neo$^r$ cell populations emerge from rare infection events.

Forty CEMss clones integrating and expressing the F12-HIV nef– (as) genome were isolated and cultured in order to perform a comparative molecular characterization. The Eco RI pattern of two representative clones (nos. 40 and 41) is shown in FIG. 4III. No significant differences in HIV RNA or protein patterns were detected among CEMss clones (as assessed by the variation in the integration sites).

PolyA+ RNAs were hybridized with either F12-HIV specific probes, i.e., full-length, U3-LTR, nef, and env, or with the probes shown in FIG. 3 that recognize different regions of the N2 vector. FIGS. 9a–d are Northern blots of polyA+ RNA from F12 cells (lane 1), parental CEMss cells (lane 2), and N2/F12-HIV nef– (as) transduced CEMss clone 40 (lane 3) hybridized with full-length F12-HIV (FIG. 9a), F12-HIV U3 LTR (FIG. 9b), F12-HIV nef (FIG. 9c), and F12-HIV env probes (FIG. 9d), i.e., F12-HIV-specific probes. Molecular weights of the F12-HIV major RNA species are indicated on the left of the figures. For each of the Northern blots shown in FIG. 9, 5 $\mu$g of RNA were run in each lane of the gel used to generate the blot. F12-HIV nef– expressing CEMss clones expressed low levels of the double-spliced HIV RNAs, i.e., messengers specific for the regulatory proteins, as reported in F12HIV expressing HeLa CD4+ clones (Federico et al. (1995), supra). In contrast, full-length and single-spliced RNAs were transcribed quite efficiently. The doublet clearly detectable in the higher molecular weights corresponded to the two full-length transcripts promoted in opposite orientations by the F12-HIV and the MLV 5'LTRs. This observation was supported by the single, instead of double, band at about 11 kb detected by hybridizing the same polyA+ RNAs with a probe overlapping the U3 region of the F12-HIV LTR, which could only be transcribed from the DNA chain encoding the N2 retroviral vector.

FIG. 10a–d are Northern blots of polyA+ RNA from F12 cells (lane 1), CEMss cells transduced with a double-promoted retroviral vector pLj (lane 2, Korrnan et al., PNAS USA 84: 2150–2154 (1987)), and N2/F12-HIV nef– (as) transduced CEMss clone 40 (lane 3) hybridized with neo (FIG. 10a), U3-MLV (FIG. 10b), R/U5-MLV (FIG. 10c), and MLV (FIG. 10d) N2-specific probes. Molecular weights of the major RNA species produced in CEMss by the pLj vectors are reported on the left-hand side of the Northern blots. The hybridization of the polyA+ RNA with probes specific for the neo gene, the U3 and R-U5 regions of the N2 LTR, and the N2 site showed that single- and double-spliced transcripts promoted by the F12-HIV 5'LTR were recognized by each probe, indicating that these RNA species were transcribed up to the U3 region of the MLV 5'LTR. The single high molecular weight band obtained after hybridization with the N2 site-specific probe, which necessarily recognizes the N2 5'LTR-promoted transcript, indicated that unspliced F12-HIV RNA did not include such sequences, suggesting a splicing event that, instead, did not occur in the single- and double-spliced F12-HIV RNAs. No spliced RNAs were transcribed by the MLV 5'LTR. In fact, no additional RNA bands were detected beside the doublet at 10–11 kb and the single- and double-spliced F12-HIV mRNAs, which are more easily seen only after a film overexposure. Accordingly, as shown in FIG. 9, a single high molecular weight signal was detected by hybridizing CEMss polyA+ RNA with the F12-HIV U3/LTR probe that solely recognizes the N2 5'LTR-promoted transcripts.

Figure 14:
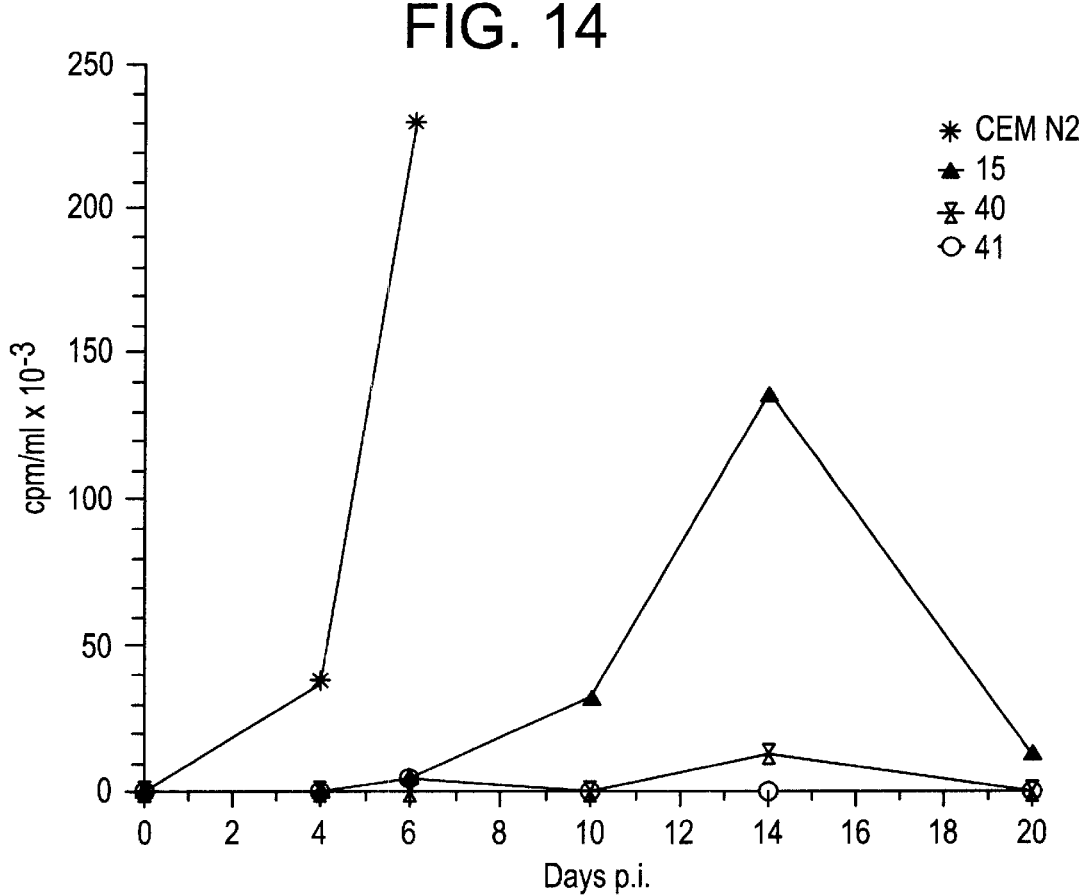
Figure 14A:
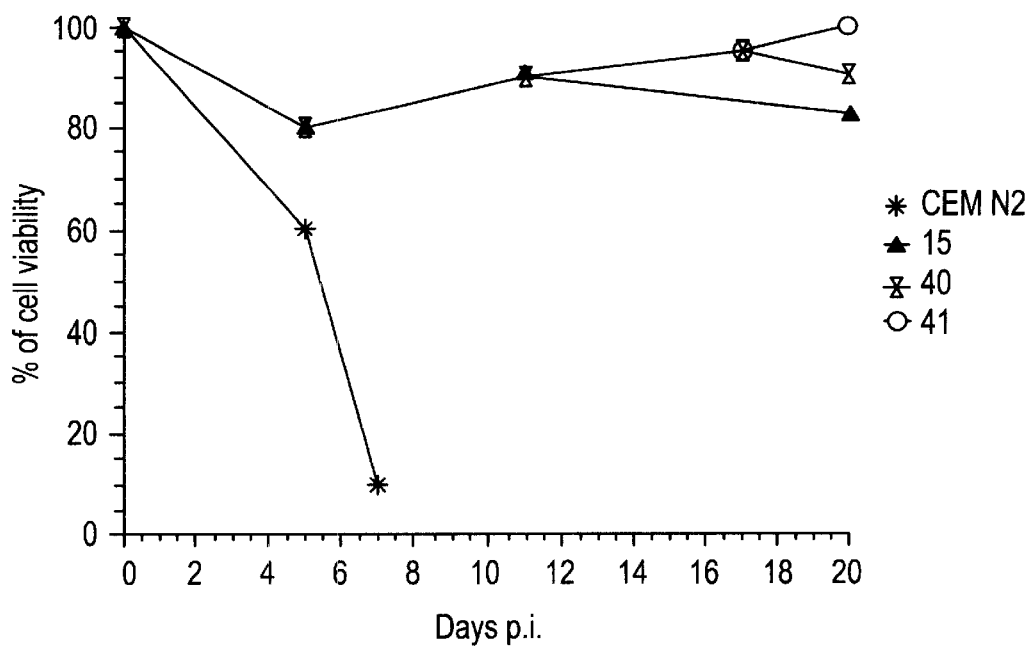

The viral protein profile produced by the N2/F12-HIV nef– (as) transduced CEMss clones was similar to that obtained in F12-HIV-transfected HeLa CD4+ clones (Federico et al. (1995), supra). FIG. 14a is a graph of cpm/ml of culture supernatant x 10-3 versus days post-infection (p.i.) and FIG. 14b is a graph of % of cell viability versus days p.i. for representative N2/F12-HIV nef– 9 (as) CEMss transduced clones, i.e., 15, 40 and 41, superinfected with $10^5$ TCID$_{50}$/$10^6$ cells. N2 transduced cells were utilized as a control. No cleavage of the gp 160 env glycoprotein was detected, whereas reduced amounts of p55 and p25 gag proteins were observed, in comparison to cells infected with a replication-competent HIV. Except for clone 21, no significant reduction of CD4 expression was detected in any F12-HIV nef– expressing CEMss clone as shown in Table III.

TABLE III

CD4 FACS Analysis of N2/F12-HIV nef– transduced CEMss Clones

| Cell Clone | % of CD4+ cells | Mean Fluorescence Intensity |
|---|---|---|
| CEM N2 | 99.55 | 491 |
| F12 | 1.99 | <10 |
| 5 | 89.55 | 501 |
| 15 | 95.81 | 431 |
| 17 | 69.17 | 384 |
| 21 | 29.21 | 138 |
| 22 | 93.25 | 488 |
| 28 | 97.03 | 530 |
| 31 | 97.03 | 436 |
| 35 | 99.31 | 528 |
| 40 | 85.63 | 509 |
| 41 | 92.23 | 465 |

Figure 12A:
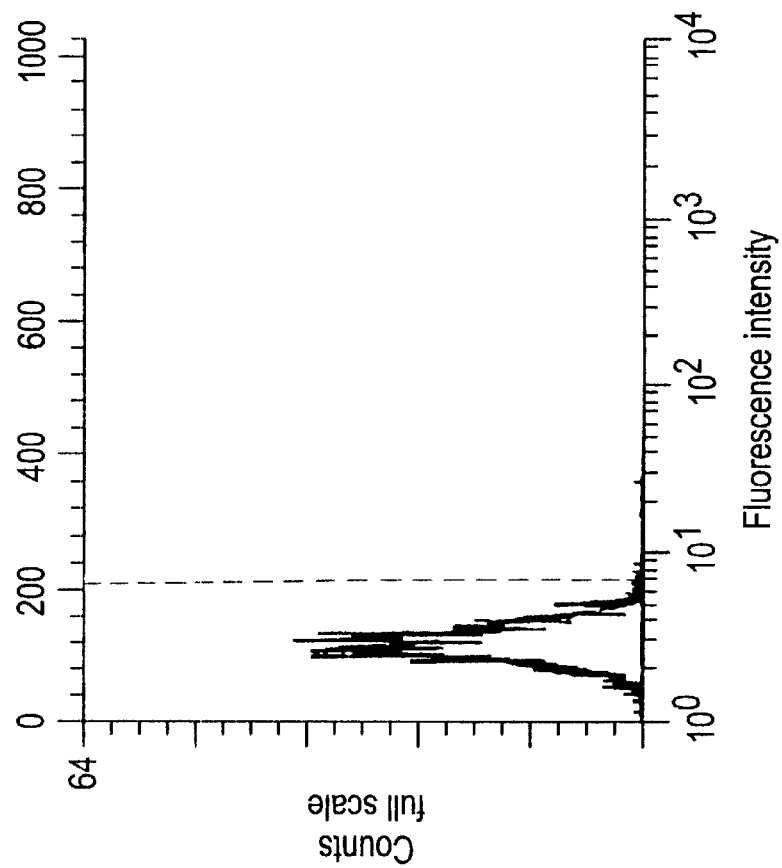
Figure 12B:
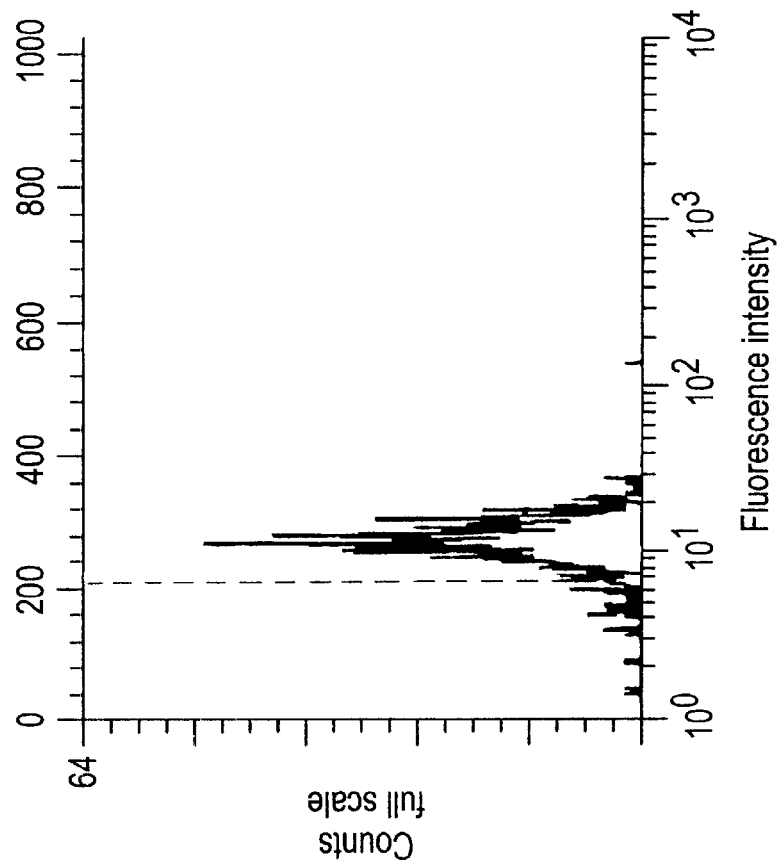
Figure 12C:
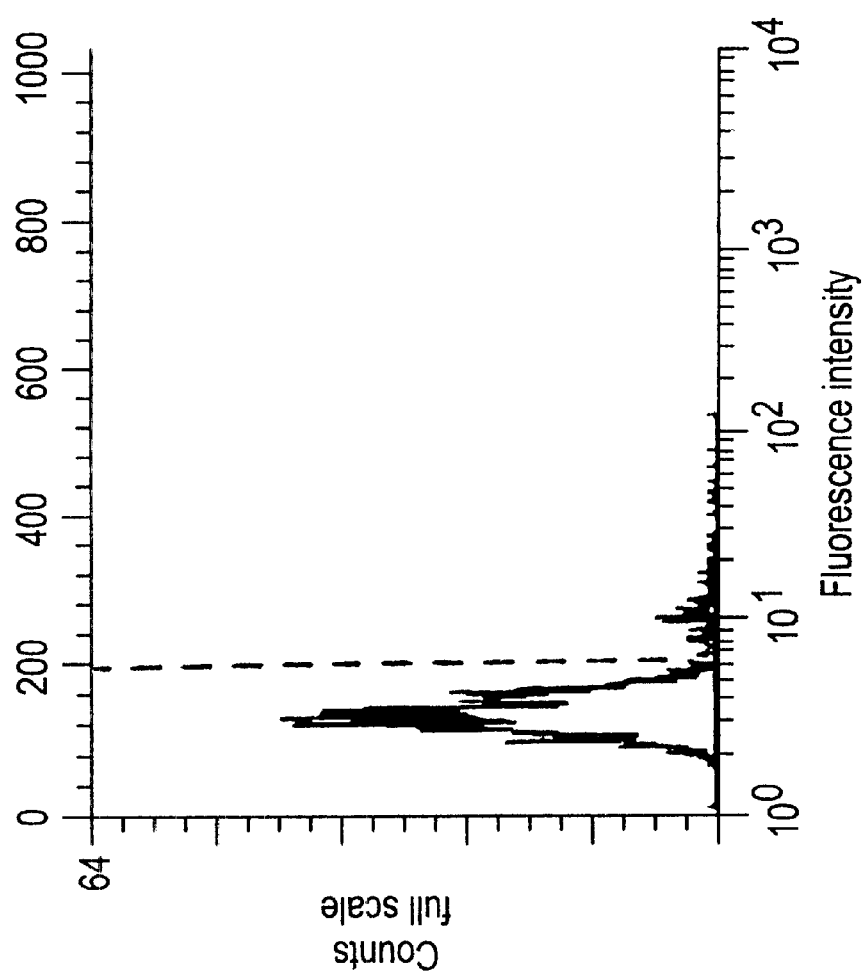

The N2/F12-HIV nef– (as) construct was also transduced into fresh human peripheral blood lymphocytes (PBLs). After 24 hrs of cocultivation, the transduction efficiency was assessed by testing the intracytoplasmic extracts by ELISA. The gag protein was obtained in amounts of 15 and 39 pg, respectively, from $10^5$ PBLs 5 days after the termination of cocultivation with PA317 clones nos. 2 and 12. Accordingly, it was estimated by FACS analysis that about 5% of PBLs were successfully transduced by the cocultures as shown in FIGS. 12a–c. FIGS. 12a–c are graphs of counts full scale versus fluorescence intensity representing FACS analysis of anti-gag HIV treated HUT78-F12 cells (FIG. 12a, positive control), uninfected PBLs (FIG. 12b, negative control), and fresh human PBLs 5 days after termination of cocultivation with PA317 clone no. 12 (FIG. 12c). Percentages of positive cells are 96%, 0.7% and 5.95%, respectively. These data were supported by Southern analysis of the high molecular weight DNA extracted from transduced PBLs.

EXAMPLE 7

Molecular Characterization of Transduced CEMss Clones Superinfected with HIV

Twenty-five CEMss clones were superinfected with HIV-1, either the $HTLV_{IIIB}$ or NL4-3 strain, at a multiplicity of infection (m.o.i.) of $5 \times 10^3$ or $5 \times 10^5$ $TCID_{50}/10^6$ cells. The cytopathic effect (c.p.e.) of the HIV-1 superinfection was scored in terms of syncytia formation and cell viability. In addition, the reverse transcriptase (RT) activity of the supernatants was measured.

Figure 13:
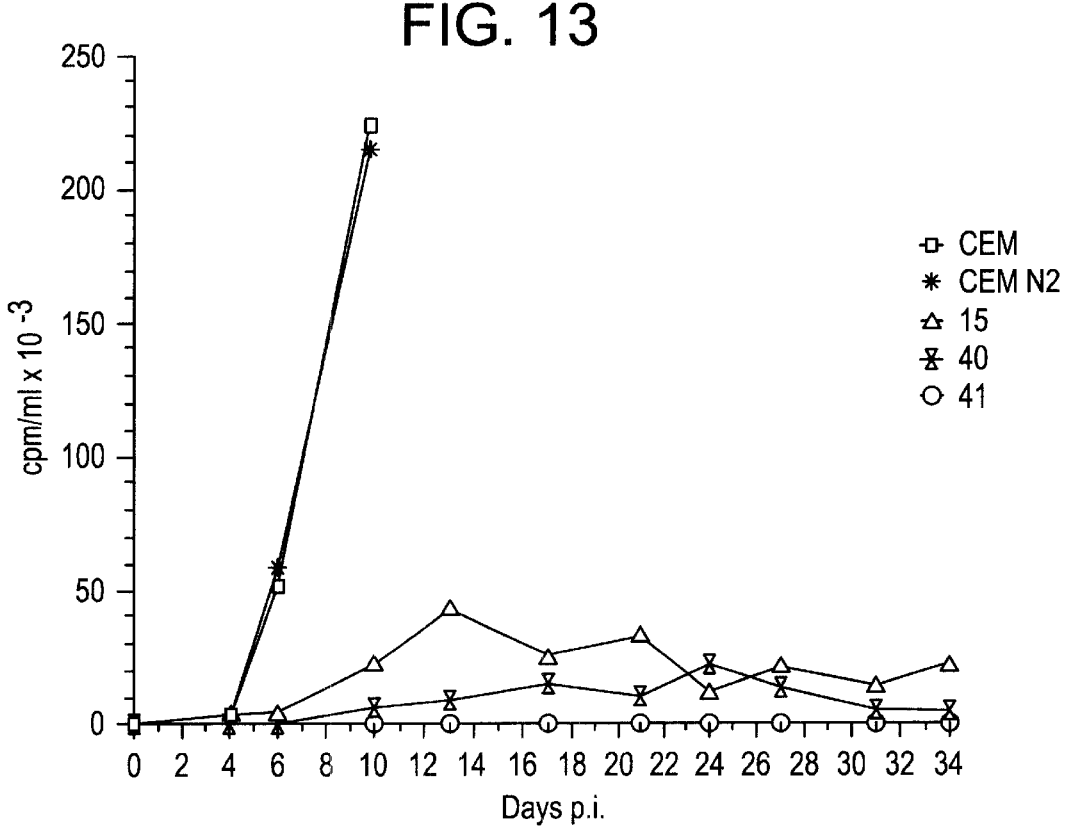

No syncytia formation was detected in any of the HIV-superinfected CEMss clones. In contrast, both wild-type CEMss and CEMss cells integrating the N2 vector rapidly formed large syncytia and died a few days after the HIV superinfection. The kinetics of both RT activity and cell viability of three representative CEMss clones are shown in FIGS. 13 and 14.

Figure 13A:
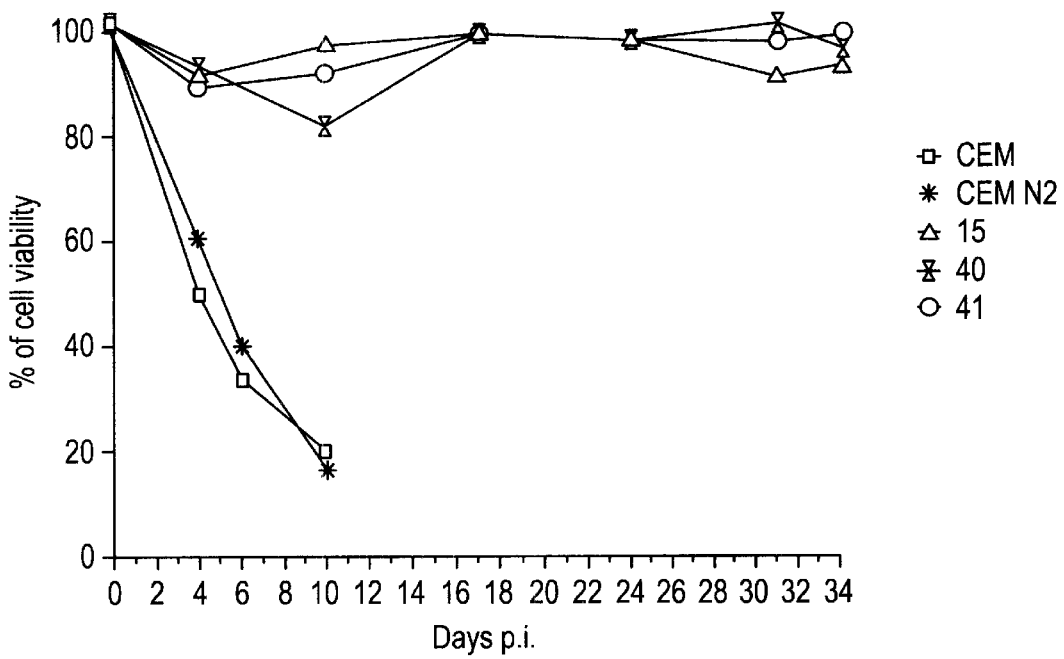

FIG. 13a is a graph of cpm/ml of culture supernatant x 10-3 versus days postinfection (p.i.) and FIG. 13b is a graph of % of cell viability versus days p.i. for representative N2/F12-HIV nef– (as) CEMss transduced clones, i.e., 15, 40 and 41, superinfected with $5 \times 10^3$ $TCID_{50}/10^6$ cells. Both parental CEMss and N2 transduced CEMss cells were utilized as controls. FIG. 14 is as described above.

The data show that HIV superinfection did not significantly affect the growth of the F12-HIV-expressing clones, even at the higher m.o.i. The positive points detected in the RT assay of clone 15 at the higher m.o.i. were representative of the few RTpositive samples originating from 5 out of the 25 transduced CEMss clones superinfected at the same m.o.i. However, in the remaining CEMss clones, very low or negative RT values were detected, regardless of the m.o.i. used and the number of days after superinfection.

Thus, the expression of the F12-HIV genome strongly inhibited the replication of a wild-type super-infecting HIV, without affecting the CD4 HIV receptor exposure. The interfering property was thus also preserved when the F12-HIV genome lacking its nef gene was inserted into the N2 vector and transduced by recombinant retroviral infection (see, also, Federico et al. (1995), supra).

All of the references cited herein, including patents, patent applications, journal articles and books, are hereby incorporated in their entireties by reference.

While this invention has been described with an emphasis upon one or more preferred embodiments, it will be obvious to those of ordinary skill in the art that variations can be employed, including variations that result from improvements in the art, and that the invention can be practised in other ways than as specifically described herein. Accordingly, this invention includes all such variations and modifications encompassed within the spirit and scope of the invention as defined by the following claims.

What is claimed is:

1. A composition comprising a recombinant retroviral expression vector comprising a replication-defective, nonproducing, interfering, modified human immunodeficiency virus type 1 (HIV-1) F12 proviral genome, wherein said F12 proviral genome has been modified by deletion of the 3'LTR and a portion of the nef coding region, and said genome is inserted into the expression vector in an antisense orientation with respect to the transcription direction of the vector, wherein said recombinant vector is capable of stably transfecting or transducing the modified provirus into CD4+ human cells and expressing the F12 proviral genome in quantities sufficient to confer resistance to HIV-1 or HIV-2 superinfection of said CD4+ human cells.

2. The composition of claim 1, wherein said retroviral expression vector is selected from the group consisting of N2, pLj, LSXN, and NSV.

3. The composition of claim 1, wherein said modified HIV-1 F12 proviral genome is capable of stably integrating into at least 1% of said cells.

4. The composition of claim 3, wherein said modified HIV-1 F12 proviral genome is capable of stably integrating into 1–10% of said cells.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 6 base pairs
      (B) TYPE: nucleic acid
      (C) STRANDEDNESS: single
      (D) TOPOLOGY: linear (xi) SEQUENCE DESCRIPTION: SEQ ID NO: 1:

AACCAA

```
(2) INFORMATION FOR SEQ ID NO: 2:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (xi) SEQUENCE DESCRIPTION: SEQ ID NO: 2:

AATAAA                                                                          6

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 3:

GGCAAGCTTG GTTGAGGCTT AAGCAGT                                                   27

(2) INFORMATION FOR SEQ ID NO: 4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 4:

ATGGATGACC CGGGGAGAAG AGAAAA                                                    26
```